United States Patent [19]

Castor

[11] Patent Number: 5,750,709
[45] Date of Patent: May 12, 1998

[54] METHOD AND APPARATUS FOR ISOLATING THERAPEUTIC COMPOSITIONS FROM SOURCE MATERIALS

[75] Inventor: Trevor P. Castor, Arlington, Mass.

[73] Assignee: Aphios Corporation, Woburn, Mass.

[21] Appl. No.: 381,456

[22] Filed: Jan. 31, 1995

Related U.S. Application Data

[63] Continuation-in-part of Ser. No. 30,696, Mar. 12, 1993, Pat. No. 5,440,055.

[51] Int. Cl.$^6$ .................. C07D 211/70; C07D 207/06; C07D 409/00

[52] U.S. Cl. ..................... 546/348; 548/579; 549/60

[58] Field of Search ................... 549/60; 548/579; 546/348

[56] References Cited

U.S. PATENT DOCUMENTS 5,440,055  8/1995  Castor .................... 549/510

Primary Examiner—Joseph Conrad

[57] ABSTRACT

Method and apparatus are described for isolating natural therapeutic compositions from source materials. The method and apparatus isolate natural therapeutic compositions from waxes, fats, oils and other constituents of the source material with the use of supercritical, critical or near critical fluids.

21 Claims, 6 Drawing Sheets

METHOD AND APPARATUS FOR ISOLATING THERAPEUTIC COMPOSITIONS FROM SOURCE MATERIALS

This application is a continuation-in-part of U.S. Ser. No. 08/030,696 filed Mar. 12, 1993, now U.S. Pat. No. 5,440,055.

FIELD OF THE INVENTION

The present invention relates to methods and apparatus for extracting and purifying therapeutic compositions from source materials. The method and apparatus feature supercritical, critical and near critical fluids to extract and purify compounds having pharmacological activity from source material comprising plants, marine life-forms, and animals and other biomass.

BACKGROUND OF THE INVENTION

Numerous compounds showing pharmacological activity have been identified in the organic solvent extracts of plant material, microorganisms, marine organisms, and animals and other biomass. Further investigation into the utility of these compounds in therapy agents has been hampered by their low natural natural abundance and the inefficiencies of conventional extraction techniques. An example of one such compound is paclitaxol, also known as taxol, (NSC 125973), a diterpene plant product derived from the western yew *Taxus brevifolia*. This drug, currently in clinical trials, has exhibited a striking 30 to 40% response rate against advanced cases of ovarian and a number of other cancers. This drug is, however, in short supply.

Currently, paclitaxol is extracted with organic solvents from the milled bark of *T. brevifolia* in three major steps and chromatographically purified in four major steps. The extraction process begins with milled bark which is percolated three times with methanol at 50° to 55° C. The extract is then concentrated in methanol. Next, the concentrated methanol extract is partitioned between methylene chloride and water. The methylene chloride fraction, containing paclitaxol, is concentrated. The methylene chloride concentrate is dissolved in 50/50 acetone:hexane, and the mixture is filtered to remove insolubles. This organic extraction process yields an amber colored syrup with a solids content which is about 1.3% of the milled bark.

The conventional purification is performed in four major steps. First, the acetone:hexane mixture from the extraction process is chromatographed on Florisil columns in a 70/30 hexane:acetone mixture to separate the paclitaxol containing fractions. The paclitaxol fractions are then concentrated to dryness. This step may be repeated as many as nine times. Second, paclitaxol concentrates are crystallized from a methanol:water mixture and then recrystallized from an acetone:hexane mixture yielding 85 to 95% pure paclitaxol. Third, the paclitaxol is chromatographed on silica gel packed with either 2.5% isopropanol or 2.5% n-butanol in methylene chloride to yield approximately 98% pure paclitaxol. Fourth, the paclitaxol is dissolved in acetone, the solution filtered, and paclitaxol recrystallized from an acetone:hexane mixture.

This organic phase extraction and chromatographic purification process yields 99% pure paclitaxol which is about 0.014% of the milled bark. The production of paclitaxol by this technique is encumbered by the following: (i) time consuming extraction and purification procedures; (ii) long residence times in a harsh environment; and (iii) low overall yields. Also the bark of *T. brevifolia* is usually obtained from mature trees (100 to 200 years old). The bark is difficult and costly to harvest, and is in limited supply. That tree is in danger of extinction. A significant amount of research is being conducted to find alternate manufacturing routes and raw material sources. Some of the alternate manufacturing routes include total synthesis and semi-synthesis from a closely-related taxoid, 10-deacetyl baccatin III. Alternate sources include needles of the ornamental yew, twigs, sprouts and plant cell cultures. With the exception of total synthesis which has not yet been accomplished and which may prove difficult to commercialize, these techniques all require extraction and purification of taxoids from a biomass source.

The needle of the ornamental yew may prove to be a very attractive raw material resource. The needle contains high quantities of taxoids, and is a renewable resource which can be readily cultivated in nurseries and farms.

However, the needles present additional processing challenges. The needles contain a significant amount of waxes and nonpolar constituents which are extracted into organic solvents. Some of the more nonpolar waxes can be removed by a solvent prewash with hexane. However, some compositions closely related to taxoids coextract with paclitaxol in the major conventional solvent extraction step using methylene chloride and methanol mixtures. The total mass extracted from the needles by organic solvent may range from 35 to 42% compared to 25% for the bark. The vastly larger percentage is not an indication of greater amount of paclitaxol but of the impurities which coextract. The virgin needles also contain a substantial amount of water (about 60%).

The paclitaxol extraction and purification steps for needles thus become much more complicated and time consuming than the previously described process for bark.

Vincristine and vinblastine, used in chemotherapeutic regimes for child-hood leukemia, are extracted and purified from the leaves of an ornamental plant—*Catharanthus roseus*, more commonly called the Madagascar or "rosy" periwinkle.

Etoposide and teniposide, effective DNA-topoisomerase inhibitors and potent chemotherapeutic agents, are derivatives of podophyllotoxine which is extracted from the North American plant Podophyllum pelatum Linnaeus or the Indian species p. emodi.

A further example of a natural therapeutic composition is camptothecin. Derived from the plant *Camptotheca acuminata*, camptothecin is an inhibitor of topoisomerase I, an enzyme involved in the replication of DNA. Tumor cells display a higher level of this key enzyme than normal cells. Camptothecin acts to form breaks in the DNA at the site of enzyme activity, leading to cell death. In Phase II clinical studies, camptothecin derivatives showed activity against carcinomas of the stomach, colon, head, neck, and bladder.

Bryostatin-I is in Phase II clinical trials as an antileukemic agent at the Cancer Research Campaign (UK) and the National Cancer Institute. In addition to its anti-tumor activity, bryostatin I has been shown to have selective beneficial effects on the bone marrow, normally a site of toxicity. Scarce supplies of *Bugula neritina*, the marine biosource, and low extraction yields are limiting the supply of the compound for clinical studies.

*Bugula neritina* is found in temperate and subtropical environments worldwide. However, only *B. neritina* from California and the Gulf of Mexico is known to contain bryostatins 1, 2 and 3 that are characterized by the C-20 (E,E)-octa-2-dienoate ester (Pettit et al., 1985).

Development of the bryostatins, originally discovered in 1968, has been hampered by available drug supply. All preclinical and clinical supplies of the drug have come from wild-collected biomass that contains variable amounts of bryostatin 1 at very low concentrations (around $10^{-6}\%$). The bryozoan, which is commonly known as a "moss animal," is laboriously scraped off rocks at depths greater than 10 meters. The purity and impurities of the bryostatin 1 clinical supplies have also been difficult to control since the total and relative yields of the closely-related bryostatins are quite variable from population to population, and because contaminating organisms (e.g. sponges and algae) cannot be excluded from wild-grown materials.

The extraction and purification process now employed for bryostatin is time consuming, utilizes significant quantities of organic solvents, and is subject to losses in yield due to inherent process efficiencies.

Michellamine-B is a potential anti-HIV agent isolated from the leaves of the Cameroon vine *Ancistrocladus korupensis*, which grows in the Korup region of Cameroon. Michellamine-B, a unique dimeric naphthalene tetrahydroisoquinoline alkaloid. Michellamine-B inhibits the cytopathic effects of HIV. Michellamine-B has recently passed NCI's Decision Network for clinical evaluation.

Other examples include halomon, a unique pentahalogenated monoterpene isolated from the red alga *Portieria hornemanni*. Halomon exhibits cytotoxicity against brain, renal and colon tumor cell lines.

Ecteinascidin is a compound demonstrating potent DNA binding activity. Ecteinascidin is isolated from the Caribbean tunicate, *Esteinascidia turbinata*.

Typically, processes for isolating natural therapeutic compositions are time consuming and yields are low. For example, counter-current chromatography steps, often applied in these processes, require 12 to 14 hours, and produce limited yields.

These processes require the use of large volumes of toxic organic solvents to extract the active pharmological compositions. Additionally, the toxic solvents used are not readily recyclable and require expensive disposal. These techniques usually require the siting of a fixed plant of sufficient size to realize economies of scale. Such a fixed plant is further encumbered by logistics and transportation costs if they are located at a significant distance away from, and probably in a different continent than, the low-grade biomass raw materials.

Natural therapeutic compositions often occur in limited or trace quantities. Harvesting the raw materials containing such limited amounts can be problematic when large quantities of the active agent are required for preclinical trials and clinical development.

The difficulties are not limited to these specific examples. Natural therapeutics share common difficulties including the isolation of the composition from waxes, fats, and oils.

SUMMARY OF THE INVENTION

Embodiments of the present invention are directed to methods and apparatus for extracting and purifying natural therapeutic from source materials having waxes, fats or oils and other constituents. The embodiments of the present invention have particular application in extracting taxoids, such as paclitaxol, from the needles of the yew tree; alkaloids, such as vincristine, vinblastine, camptothecins, and michellamine-B; lactones, such as bryostatin 1; and terpenes, such as halomon. The embodiments feature critical, supercritical or near critical fluid.

As used herein, the term "critical fluid" refers to a fluid at or above its critical pressure and at or above critical temperature. A supercritical fluid refers to a fluid which is above its critical pressure and above its critical temperature. Thus, the term "critical fluid" encompasses the subject matter of the term "supercritical fluid." The term "near critical fluid" refers to a fluid which approaches but is not at the critical pressure and/or critical temperature; and in particular such fluids which are at or above critical pressure but below critical temperature. Near critical fluid is used to denote a fluid which has a density which is similar to that of a critical fluid. This application will use the term "SCoCoNC fluid" for convenience in referring to supercritical, critical or near critical fluids.

As used herein, the term "natural therapeutic" refers to compounds and compositions which exhibit pharmacological activity, or which are processed to make compounds or compositions which exhibit pharmacological activity, which compounds are isolated from plant, animal, bacterial, fungal, yeast or protozoan sources. Examples of natural therapeutics comprise, without limitation, alkaloids such as vincristine, vinblastine, camptothecin, and michellamine-B; lactones, such as bryostatin-I, and terpenes, such as halomon, taxoids, etoposide, teniposide, and ecteinascidin.

As used herein, the term "wax" refers to natural unctuous, viscous or solid heat sensitive substances consisting essentially of high molecular weight hydrocarbons. The term "fat" refers to various soft solid or semisolid organic compounds comprising the glyceride esters of fatty acids, and associated phosphatides, lipids sterols, alcohols, hydrocarbons, ketones and related compounds. The term "oils" refers to hydrocarbon substances of lower molecular weight than waxes exhibiting liquid behavior at room temperature and soluble in organic solvents.

The term "source material" is used to denote biomass potentially containing the natural therapeutic compositions. The term "biomass" is used in the sense of material derived from living organisms.

One embodiment of the present invention features a method of extracting natural therapeutic compositions from source materials. The method has particular application where the source materials have waxes, fats, oils and other constituents which may coextract with natural therapeutic compositions in conventional solvent extraction techniques. The method comprises the steps of subjecting the source material to deoiling, dewaxing, or defatting conditions. Deoiling, dewaxing or defatting conditions comprise subjecting the source material to a first fluid. The first fluid is a nonpolar SCoCoNC fluid. The waxes dissolve in the first fluid to form a wax or fat or oil laden extractant and a deoiled, dewaxed and defatted source material. The method further comprises the step of removing the natural therapeutic from the deoiled, dewaxed and defatted source material by subjecting the deoiled, dewaxed and defatted source material to a second fluid to form a natural therapeutic composition extractant and residual material. The second fluid is a mixture of a SCoCoNC fluid and a polar cosolvent. The oil, wax or fat laden extractant and the natural therapeutic composition extractant are subjected to chromatography means to form a natural therapeutic composition and one or more eluant.

As used herein, the term "nonpolar" suggests a material with a dipole movement of 0.0 to 0.1 Debyes. The term "polar" suggests a material with a dipole movement of approximately 0.1 to 0.1 to 1.7 Debyes.

Preferably, eluants are depressurized to separate natural therapeutic composition that have coeluted. Natural therapeutic compositions which coelute precipitate from the SCoCoNC fluid upon depressurization. Natural therapeutic compositions, isolated upon depressurization of the SCoCoNC fluid, are purified by chromatographic techniques to form purified compounds.

Preferably, the depressurized first and second fluids are passed through an extractant cooler to form a SCoCoNC fluid substantially free of natural therapeutic compositions which is then recycled, and waste, which is removed.

The term "substantially free of natural therapeutic compositions" is used in the sense of having less of the natural therapeutic composition compared to the starting material of the process step.

Chromatography means comprise one or more chromatographic columns. Natural therapeutic compositions absorbed on a first column, during the passage of second fluid, are eluted with a relatively polar mixture of an organic solvent (hexane:n-propanol:methanol ternary gradient) or a third fluid. The third fluid is comprised of a SCoCoNC fluid and a cosolvent of different type or concentration that the second fluid. Fractions which are identified as containing large amounts of natural therapeutic compositions are subjected to further chromatography with additional columns. Fractions which are identified as containing nontaxoids or small amounts of natural therapeutic compositions are treated as waste or reprocessed and recycled as an elutant through additional chromatographic processes. Fractions with small amounts of the natural therapeutic composition, which are not waste, are subjected to a fourth fluid. The fourth fluid is comprised of a SCoCoNC fluid and a polar cosolvent. The pressure and/or the temperature of fourth fluid is either higher or lower than the third fluid to remove nonnatural therapeutic composition solutes. Thereafter, the temperature and pressure of the fourth fluid is adjusted and the fluid recycled through the first chromatography column.

Natural therapeutic composition containing fractions are subjected to further columns and are then eluted by a relatively nonpolar mobile phase comprising an organic solvent mixture or fifth fluid. The fifth fluid is comprised of a SCoCoNC fluid and a nonpolar cosolvent. Suitable organic solvent mixtures comprise methanol, acetone, acetonitrile ethylacetate, hexane and methylene chloride mixtures. Fractions containing purified natural therapeutic compositions and closely related compounds are collected. The mobile phase containing no natural therapeutic composition or small amounts of the natural therapeutic composition are sent to waste or reprocessed and recycled. SCoCoNC fluid/solvent mixtures with no identifiable natural therapeutic composition are reprocessed by changing the pressure and the temperature of the mixture to allow impurities to leave the solution to produce a SCoCoNC fluid and SCoCoNC fluid/mixture cosolvent suitable for recycling.

Preferably, the SCoCoNC fluid is selected from the compounds carbon dioxide; nitrous oxide; alkanes, such as propane; alkenes, such as ethylene; and fluorocarbons, such as chlorodifluoromethane. These compounds are gases at normal room temperatures and pressures. However, at low temperatures, and pressures above atmospheric pressure, these compounds have the ability to form SCoCoNC fluids.

Preferably, polar cosolvents are selected from the group of polar solvents consisting of methanol, ethanol, butanol, propanol, methylene chloride, and acetone.

Embodiments of the present method are ideally suited to extract taxoids consisting of paclitaxol, cephalomannine, baccatin III, 10-deacetyl baccatin III, deacetyltaxol and deacetyl-7-epitaxol and derivatives and precursors thereof.

Embodiments of the present method are also ideally suited to extract and purify vincristine, vinblastine, camptothecin, michellamine-B, bryostatin-I, halomon, etoposide, teniposide ecteinascidin and closely related compounds. Embodiments of the present invention allow for the isolation and extraction of natural therapeutic compositions from a renewable source material such as needles, leaves, stems, bark, roots, vines, and other biomass.

Optionally, the biomass is first dried to remove water and processed to expand the effective surface area of the material. Typical processing to expand the surface area comprises grinding or milling.

One embodiment of the present invention features an apparatus for extracting natural therapeutic compositions from source materials having waxes, fats or oils and other constituents. The apparatus comprises a chamber adapted to receive source materials, a first fluid, and a second fluid. The apparatus further comprises a source of a first fluid in communication with the chamber. The first fluid comprises a SCoCoNC fluid. The source of first fluid is capable of directing a first fluid into the chamber to subject the source material to dewaxing, defatting or deoiling conditions. The first fluid dissolves the waxes, fats or oils of the source material to produce a wax, fat or oil containing extractant and a dewaxed, defatted or deoiled source material. The apparatus further comprises a source of a second fluid. The second fluid is a mixture of a fluid and a polar cosolvent. The source of the second SCoCoNC fluid is in communication with the chamber. The source of the second fluid is capable of directing the second fluid into the chamber to form a natural therapeutic composition extractant and waste material. The chamber is in communication with chromatography means for receiving the wax, fat or oil laden extractant and the natural therapeutic composition extractant from the chamber to form a eluant and concentrated natural therapeutic compositions.

Preferred chromatograph means comprise one or more columns. Preferably, the columns are in communication with depressurization means to reduce the pressure of the eluant. Upon depressurization, natural therapeutic compositions, which coeluted with the eluant, are released and can be further processed.

Preferably, natural therapeutic compositions produced upon passage through the depressurization means are purified to form a purified natural therapeutic composition.

Preferably, depressurization means is in communication with an extractant cooler for receiving the eluant from the depressurization means. Upon cooling, impurities are removed from the eluant and the eluant can be recycled.

Preferably, the first and second fluids are recycled after removal of the natural therapeutic composition and waste materials by conduits and pump means in communication with the chromatography means.

One embodiment of the present apparatus features a conduit in communication with one or more columns of the natural therapeutic composition purification means and in communication with the source of the first fluid or the second fluid. The conduit is adapted to receive the second fluid flowing through the columns until natural therapeutic compositions elute. The apparatus further comprises means for directing the second fluid from such conduit, to a second column as the natural therapeutic composition elutes, to remove such natural therapeutic composition and produce a natural therapeutic composition-free SCoCoNC fluid.

Preferably, the natural therapeutic composition-free SCoCoNC fluid is depressurized allowing impurities to leave the solution to produce a second fluid suitable for recycling.

Preferably, the apparatus is adapted for receiving carbon dioxide; alkanes, such as propane; alkene, such as ethylene; fluorocarbons, such as chlorodifluoromethane; and or nitrous oxide as a SCoCoNC fluid. Preferably, the apparatus is adapted to receive a polar solvent selected from the group consisting of methanol, ethanol, propanol, butanol, methylene chloride and acetone.

The present apparatus is ideally suited for isolation of natural therapeutic compositions such as paclitaxol, baccatin III, 10-deacetyl baccatin III, cephalomannine, deacetyltaxol, deacetyl-7-epitaxol, vincristine, vinblastine, camptothecin, michellamine-B, etoposide, teniposide, bryostatin-I, halomon and ecteinascidin.

Embodiments of the present invention are able to extract 0.048 wt. % paclitaxol (99+% of available paclitaxol) from the needles of the ornamental yew with supercritical carbon dioxide containing 20.9% methanol (at 40° C. and 1,274 psia) in only 21 minutes. The paclitaxol recovery is surprising and unexpected. The short residence time is significant since it will dramatically impact the capital and operating costs of a commercial plant.

Embodiments of the present invention feature a quick high speed extraction through improved permeation and salvation. Compared to conventional methods, the process has improved production capacity and improved scalability. The process features greater overall efficiency and in fewer processing steps. Extractants made in accordance with the present invention feature improved product quality with minimal use of organic solvents.

The apparatus and method of the present invention can increase the availability of natural therapeutic compositions for research purposes and clinical trials. A preferred source material comprises needles, leaves, bark, stems, vines, roots and other plant fractures. The present method and apparatus extracts natural therapeutic compositions in the presence of impurities which may be closely related.

Other features and advantages of the present invention will be apparent from the examination of the drawings and the detailed descriptions which follow.

DETAILED DESCRIPTION OF THE INVENTION

Embodiments of the present invention will be described in detail as methods and apparatus for the extraction of paclitaxol from needles of the yew tree. As used herein, yew is intended to encompass the species Taxus media and *Taxus brevifolia*, and other plants of the genus Taxus. However, embodiments of the present invention are also applicable for the extraction and isolation of vincristine and vinblastine from *Catharanthus roseus*, etoposide and teniposide from *Podophyllum pelatum Linnaeus* or *P. emodi*, camptothecin from *Camptotheca acuminata*, bryostatin-I from *Bugula neritina*, michellamine-B from *Ancistrocladus korupensis*, halomon from *Portieria hornemanni*, and ecteinascidin from *Ecteinascidia turbinata*.

The present invention features the use of SCoCoNC fluids as solvents. SCoCoNC fluids are comprised of certain materials which exist as gases at ambient conditions, such as the gases carbon dioxide and nitrous oxide. When such gases are compressed and brought to conditions near or above their critical pressures and temperatures, such gases exhibit enhanced solvating power.

A SCoCoNC fluid exhibits a liquid-like density and at the same time gas-like properties of diffusivity and viscosity. The SCoCoNC fluid displays a wide spectrum of salvation power because its density is strongly dependent on both temperature and pressure. Temperature and pressure can be altered to change solubility by an order of magnitude or more. SCoCoNC fluids further exhibit ultralow surface tension which allows facile penetration into microporous materials.

Figures 1, 1A:
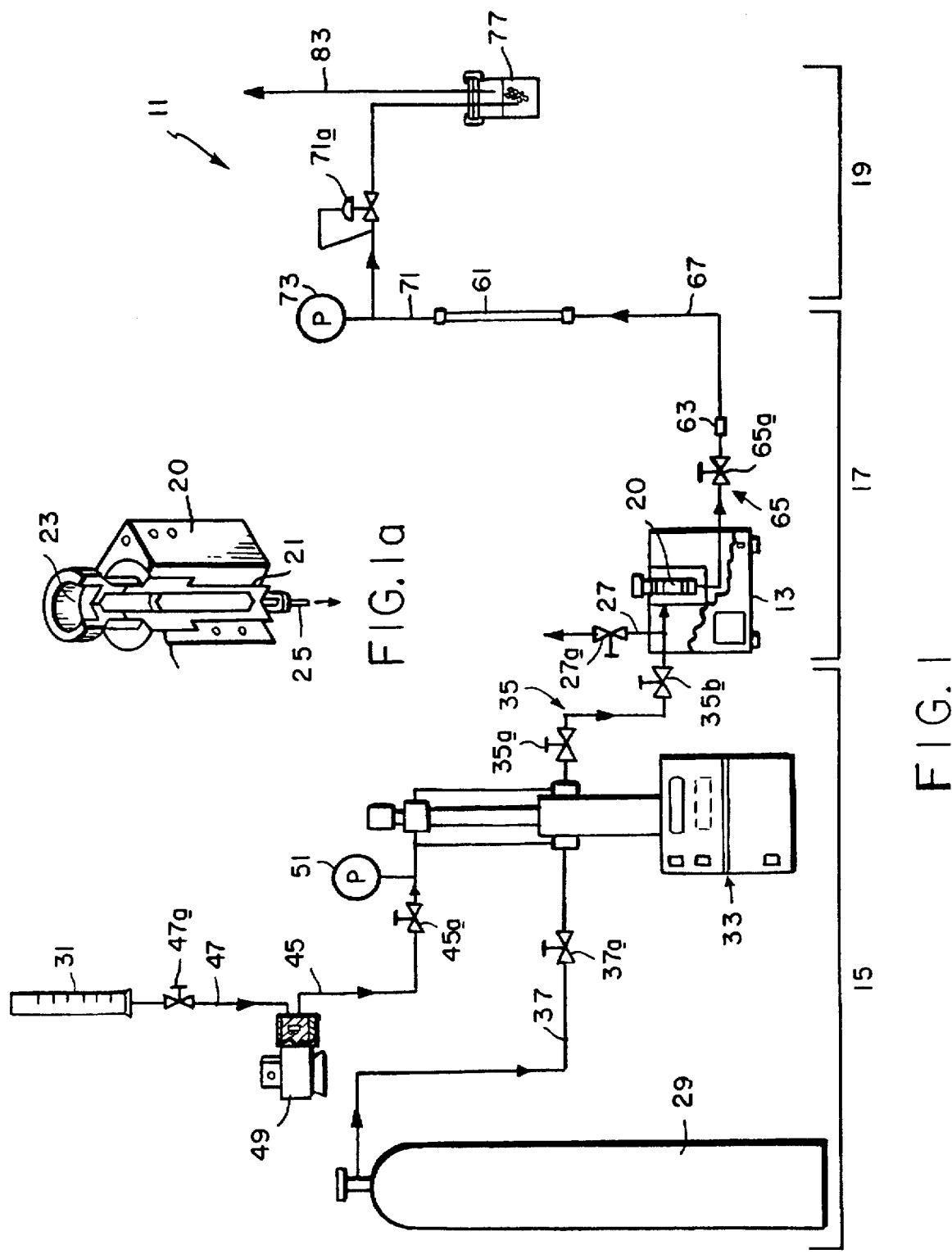
FIG. 1 depicts a schematic view of a critical fluid extraction and chromatography apparatus embodying features of the present invention.

An apparatus embodying features of the present invention for performing SCoCoNC fluid extraction of natural therapeutic compositions from source materials including needles, leaves, stems, roots, vines and other biomass, generally designated by the numeral 11, is depicted in FIG. 1. The apparatus 11 is comprised of four major elements: an extractor 13; SCoCoNC fluid delivery assembly, generally designated by the numeral 15; chromatographic purification assembly, generally designated by the numeral 17; and pressure letdown means, generally designated by the numeral 19.

The extractor 13 is depicted in greater detail in FIG. 1A. The extractor 13 has a housing 20 which defines a chamber 21 for receiving source material. Preferably, the source material has been rendered into fine particles by milling or grinding. The chamber 21 has an inlet 23 for receiving fluid and an outlet 25 for removing fluid. An extractor shunt 27, in communication with inlet 23, allows SCoCoNC fluid to be vented. The flow of SCoCoNC fluid through shunt 27 is controlled by valve 27a.

The extractor 13 is equipped with thermostatic controls (not shown) for maintaining a constant temperature and an opening (not shown) for loading source material. One such extractor is known as an Isco Model SFX 2-10 extraction unit.

The inlet 23 of chamber 21 is in communication with the SCoCoNC fluid delivery assembly 15. The SCoCoNC fluid delivery assembly 15 is comprised of the following major elements: SCoCoNC fluid vessel 29, cosolvent vessel 31 and syringe pump 33. Syringe pump 33 is in communication with the inlet 23 of chamber 21 via conduit 35. Two valves 35a and 35b control flow in conduit 35. Syringe pump 33 is adapted to receive cosolvent from cosolvent vessel 31 and a SCoCoNC fluid from SCoCoNC fluid vessel 29. Syringe pump 33 is in communication with critical fluid vessel 29 via conduit 37. A valve 37a controls the flow of SCoCoNC fluid in conduit 37.

Syringe pump 33 is in communication with cosolvent vessel 31 via two conduits 45 and 47. Conduit 45 is in direct communication with syringe pump 33 and cosolvent pump 49. The flow of cosolvent to the syringe pump 33 is controlled by a valve 45a. Pressure in conduit 45 is monitored by a pressure gauge 51.

Conduit 47 is in direct communication with cosolvent pump 49 and cosolvent vessel 31. Cosolvent is received by cosolvent pump 49 from conduit 47 and forced through conduit 45. The flow of cosolvent to cosolvent pump 49 via conduit 47 is controlled by valve 47a.

Extractor outlet 25 is in communication with chromatographic purification assembly 17. Chromatographic purification assembly 17 is comprised of two major elements, an HPLC column 61 and filter element 63. Filter element 63 is a 5 micron filter, in communication with outlet 25 via an outlet conduit 65. SCoCoNC fluid flowing from the extractor through conduit 65 is filtered by filter element 67. SCoCoNC fluid enters the HPLC column 61 via conduit 67. HPLC column 61 is a normal phase HPLC column.

The SCoCoNC fluid flows from the HPLC column 61 to pressure letdown assembly 19. SCoCoNC fluid leaves HPLC column 61 via conduit 71. Pressure within the outlet conduit 71 is monitored by a pressure gauge 73 and controlled by pressure letdown valve 71a.

The depressurized SCoCoNC fluid enters a collection vessel 77. Collection vessel 77 contains a solid or liquid entrapment phase, such as a 50:50 mixture of methylene chloride and methanol. Collection vessel 77 retains natural therapeutic compositions held in the SCoCoNC fluid, as well as any cosolvent which does not vaporize. SCoCoNC fluid is vented through a vent 83.

In operation, with reference to paclitaxol, a dried, and milled or ground source material, such as milled or ground needles of the yew tree, is placed within the chamber 21 of the extractor 13. The source material first receives a flow of a first fluid, such as SCoCoNC carbon dioxide. The first SCoCoNC fluid is relatively nonpolar. The waxes, fats, and oils and other constituents of the source material are dissolved in the SCoCoNC fluid and are removed through outlet 25 of chamber 21 and through conduit 65. The wax, fats and oils and other nontoxoid constituents of the source material held in the SCoCoNC fluid are collected in collection vessel 77 and discarded. The SCoCoNC fluid is vented through vent 83.

Next, a second fluid is formed by combining a polar cosolvent such as methanol, ethanol, or acetone, with a SCoCoNC fluid. Syringe pump 33 receives the second fluid which is injected into the extractor chamber 21 via conduit 35. The second fluid removes the natural therapeutic composition, paclitaxol, from the source material. The natural therapeutic composition laden second fluid is removed from chamber 21 through outlet 25 to the HPLC column 61 of chromatographic assembly 17. The HPLC column 61 removes the natural therapeutic composition, paclitaxol, and other natural therapeutic compositions such as 10-deacetyl baccatin-III from the second SCoCoNC fluid.

Taxoids and other impurities which coelute in the second fluid are collected in collection vessel 77. The second SCoCoNC fluid and cosolvent is depressurized at pressure letdown valve 77a, allowing the natural therapeutic compositions and other impurities to leave solution. SCoCoNC fluid is vented from the collection vessel 77 via vent 83.

Figure 2:
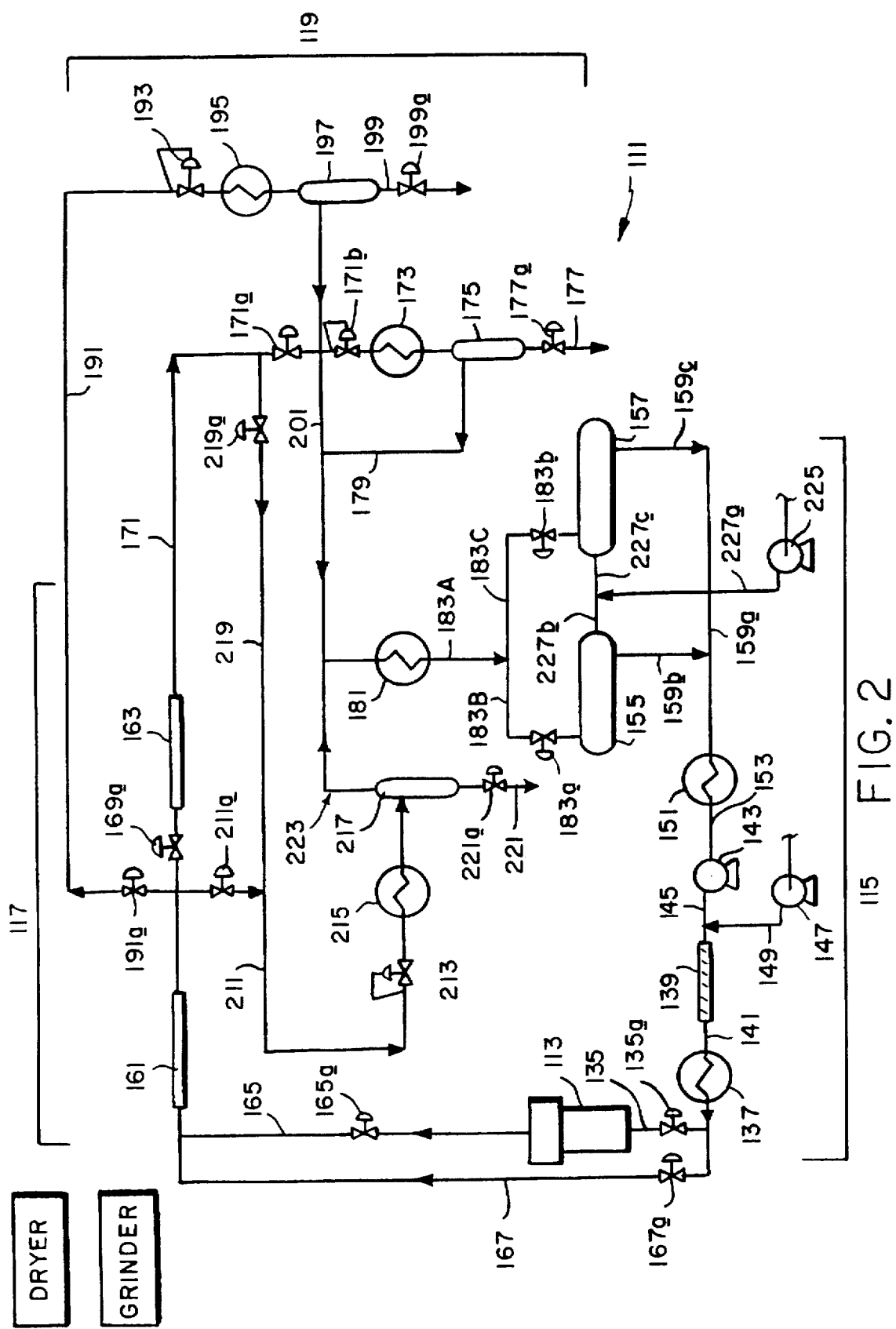
FIG. 2 depicts a critical fluid extraction and chromatography apparatus embodying the features of the present invention, including recycling of reagents, supercritical fluid and cosolvents.

An apparatus embodying features of the present invention, featuring SCoCoNC fluid and cosolvent recycling, is depicted in FIG. 2. The natural therapeutic composition extraction apparatus, generally designated by the numeral 111, is comprised of the following major elements: an extraction assembly 113; a SCoCoNC fluid assembly, generally designated by the numeral 115; chromatographic assembly, generally designated by the numeral 117; and pressure letdown assembly, generally designated by the numeral 119.

Extraction chamber 113 has features similar to features of extraction chamber 13 described with respect to FIG. 1. That is, extraction chamber 113 has an inner chamber (not shown) having an inlet and an outlet (not shown). The chamber of the extraction assembly is capable of holding source materials containing natural therapeutic compositions. Preferably, the source materials are dried and optionally reduced to particulate form by drying and grinding assemblies (not shown).

The extraction assembly 113 receives SCoCoNC fluid via conduit 135 in communication with the inlet of the chamber (not shown). Flow through conduit 135 is controlled by valve 135a. Conduit 135 is in communication with preheater 137. Preheater 137 adjusts the temperature of the SCoCoNC fluid and cosolvent mixture. Preheater 137 is in communication with static mixer 139 via conduit 141. Static mixer 139 mixes SCoCoNC fluid and cosolvent to a homogenous mixture forming a second SCoCoNC fluid.

Static mixer 139 is in communication with circulation pump 143 via conduit 145, and cosolvent make-up pump 147 via conduit 149. Cosolvent make up pump 147 is in communication with a vessel (not shown) containing cosolvent. Cosolvent pump 147 is capable of injecting cosolvent into conduit 141 to adjust the concentration of cosolvent in the SCoCoNC fluid fed to extraction assembly 113.

Circulation pump 143 is in communication with a subcooler 151 via conduit 153. Subcooler 151 is adapted to cool SCoCoNC fluid and SCoCoNC fluid/cosolvent mixtures to adjust the temperature. Subcooler 151 is in communication with a reservoir of SCoCoNC fluid 155 and a reservoir, containing a second SCoCoNC fluid comprising a SCoCoNC fluid/cosolvent mixture, via conduits 159a, 159b and 159c.

The outlet (not shown) of the chamber of the extractor 113 is in communication with chromatographic assembly 117. Chromatographic assembly 117 is comprised of the following major elements: a first adsorption column 161 and a second adsorption column 163. First adsorption column 161 is in communication with outlet (not shown) of the chamber of the extraction assembly 113 via conduit 165. Valve 165a controls the flow of the second SCoCoNC fluid in conduit 165.

First adsorption column 161 is adapted to retain paclitaxol, baccatin III, 10-deacetyl baccatin III, cephalomannine and other natural therapeutic compositions of interest extracted from source materials. First adsorption column 161 is in communication with a source of SCoCoNC fluid and SCoCoNC fluid/cosolvent mixture via shunt 167. Shunt 167 is in communication with the SCoCoNC fluid reservoir 155 and SCoCoNC fluid/cosolvent reservoir 157. Valve 167a controls fluid flow through conduit 167. Shunt 167 allows SCoCoNC fluid and SCoCoNC fluid/cosolvent mixtures to elute natural therapeutic compositions adsorbed by first adsorption column 161.

First adsorption column 161 is in communication with a second adsorption column 163 via conduit 169. Valve 169a controls movement of SCoCoNC fluid or SCoCoNC fluid/cosolvent mixtures in conduit 169. Second HPLC column 163 is in communication with pressure letdown assembly 119. Conduit 171, of pressure letdown assembly 119, receives fluid from second adsorption column 163. Flow of fluid through conduit 171 is controlled by valve 171a. Conduit 171 carries eluted natural therapeutic compositions, such as paclitaxol, and SCoCoNC fluid/cosolvent to pressure letdown valve 171b, natural therapeutic composition heater 173, and a natural therapeutic composition separator 175. The natural therapeutic composition heater 173 attenuates the first fluid and the second fluid allowing natural therapeutic compositions to separate out of solution in natural therapeutic composition separator 175.

The natural therapeutic composition such as paclitaxol is removed from natural therapeutic composition separator 175 through conduit 177. Valve 177a controls the flow of fluid through conduit 177. SCoCoNC fluid and SCoCoNC fluid/cosolvent mixtures are removed from natural therapeutic composition separator 175 via a exit line 179.

Line 179 is in communication with an extractant cooler 181. Extractant cooler 181 redensifies SCoCoNC fluid and SCoCoNC fluid/cosolvent mixtures.

Extractant cooler 181 is in communication with first fluid reservoir 155 and second fluid/cosolvent reservoir 157 via conduits 183a, 183b and 183c. First fluid reservoir 155 contains a SCoCoNC fluid. Second fluid reservoir 157 contains a second fluid comprising a SCoCoNC fluid and a cosolvent. Valves 183a and 183b control fluid movement in conduits 183A, 183B, and 183C.

The natural therapeutic composition, 10-deacetyl baccatin III, elutes from column 161 with certain SCoCoNC fluid/cosolvent mixtures. Conduit 169 is in communication with pressure letdown assembly 119 via shunt 191, used to isolate baccatin in paclitaxol extraction. Valve 191a controls the flow of fluid through shunt 191. In paclitaxol extractions 10-Deacetyl baccatin III eluted from first adsorption column 161 is directed to shunt 191.

Shunt 191 is in communication with pressure letdown valve 193, heater 195 and separator 197. Pressure letdown valve 193 reduces the pressure of SCoCoNC fluid/cosolvent mixtures. Heater 197 attenuates the SCoCoNC fluid and SCoCoNC fluid/cosolvent mixtures. The combination of lower pressure and moderate temperature in paclitaxol extractions causes 10-deacetyl baccatin III to come out of solution in separator 197.

10-Deacetyl baccatin III is removed from separator 197 via conduit 199. Valve 199a controls the movement of 10-deacetyl baccatin III from separator 197.

Separator 197 is in communication with extractant cooler 181, first fluid reservoir 155 and second fluid reservoir 157 via conduit 201. Conduit 201 is in communication with conduit 179 to recycle SCoCoNC fluid and SCoCoNC fluid/cosolvent mixtures.

First adsorption column 161 is in communication with pressure letdown assembly 119 via a second shunt 211. Valve 211a controls movement of SCoCoNC fluid and SCoCoNC fluid/cosolvent mixtures through conduit 211. Conduit 211 is in communication with a pressure letdown valve 213, extractant heater 215, waste separator 217 and shunt 219. Shunt 219 is in communication with conduit 171. Shunt 219 receives supercritical fluid and supercritical fluid/cosolvent mixtures from second adsorption column 163, for recycling. Valve 219a controls movement through conduit 219.

Conduit 211 receives substantially natural therapeutic composition-free fluid and SCoCoNC fluid/cosolvent mixtures from first HPLC column 161 and shunt 219. Pressure letdown valve 213 reduces the pressure of SCoCoNC fluid and SCoCoNC fluid/cosolvent mixtures flowing through conduit 211. Extractant heater 215 heats SCoCoNC fluid and SCoCoNC fluid/cosolvent mixture flowing through conduit 211. The reduction of pressure and addition of heat allows waste materials to come out of solution in waste separator 217.

Wastes are removed from waste separator 217 via conduit 221. Valve 221a controls movement of waste fluids through conduit 221.

Waste separator 217 is in communication with extractant cooler 181, first fluid reservoir 155 and second fluid reservoir 157, via conduit 221. Conduit 221 is in communication with conduit 179 to convey SCoCoNC fluid and SCoCoNC fluid/cosolvent mixtures to extractant cooler 181. Extractant cooler 181 densifies the fluids for recycling.

SCoCoNC fluid losses are compensated by SCoCoNC fluid makeup pump 225. SCoCoNC fluid makeup pump 225 is in communication with first SCoCoNC fluid reservoir 155 and second SCoCoNC reservoir 157 via conduits 227 a, b and c. SCoCoNC fluid makeup pump 225 is in communication with a source of SCoCoNC fluid (not shown).

In operation using supercritical fluid carbon dioxide, and paclitaxol as a model natural therapeutic composition dried raw material is ground and transferred to the extraction chamber of extractor 113. A preferred dried material is yew needles. The material is subjected to a dewaxing step using a first fluid. The first fluid comprises critical fluid carbon dioxide at a density of about 0.8 g/ml. Saturated liquid carbon dioxide at approximately 1,000 psi is drawn off from the first fluid reservoir 155 and slightly subcooled to avoid cavitation during pumping. The circulation pump 143 pressurizes the first fluid to the extraction pressure of 3,000 psi, and pumps it through a static mixer 139 and a preheater 137 which brings the carbon dioxide to the extraction temperature of 40° C. The nonpolar carbon dioxide extracts the nonpolar waxes and some natural therapeutic compositions from the raw material.

The wax laden extractant is passed through a first adsorption column 161 which retains the natural therapeutic compositions. The carbon dioxide passes through valve 211a through back pressure regulator 213. The carbon dioxide undergoes a pressure drop to about 1,100 psi and a concomitant drop in temperature.

The first fluid is reheated to about 40° C. in the extractant heater 215. Under these conditions, the density of the supercritical carbon dioxide is only about 0.2 g/ml so that the entrained waxes have little solubility and drop out in the waste recovery separator 217. The purified carbon dioxide is then passed to the extractant cooler 181 to be liquefied, and returned to the first SCoCoNC reservoir 155.

The dewaxed raw material is next subjected to a paclitaxol extraction/adsorption step using a second fluid. The second fluid comprises a mixture of supercritical carbon dioxide and a polar cosolvent, for example acetone. Second fluid is drawn from reservoir 157 by the circulation pump 143. Additional cosolvent is added to the stream to make up for losses incurred during the previous cycle. The mixed stream passes through the static mixer 139 to insure a uniform composition, and then through the preheater 137 and into the extraction vessel 113. Extraction conditions are approximately the same as used for the dewaxing step.

The extractant containing paclitaxol, natural therapeutic compositions and impurities is pumped to a first adsorption column 161 where paclitaxol and similar compounds are selectively adsorbed.

Next, the extraction chamber 113 is placed offline, to be serviced, unloaded or recharged. Taxol is eluted from the first adsorption column 161 using a third fluid. The third fluid comprises carbon dioxide and a cosolvent. The concentration of the polar cosolvent is increased in the third fluid compared to the second fluid mixture. The stream leaving the first adsorption column is directed through valve 211a until the paclitaxol/cephalomannine band is eluting, at which point the flow is diverted through valve 169a to second adsorption column 163. Second adsorption column 163, adsorbs the natural therapeutic compositions, paclitaxol and cephalomannine, and other impurities. As the supercritical fluid/cosolvent mixture also has the effect of desorbing the baccatin from the silica column, the eluant is directed through valve 191 to a separate depressurization loop where the baccatin is recovered in separator 197. The recovered baccatin will contain other materials which have passed through the silica column during this extraction step, and may require further purification before use.

Following baccatin recovery, the critical fluid/cosolvent mixture is passed through the extractant cooler 181 and then to the SCoCoNC fluid/cosolvent reservoir 157 to be recycled.

Taxoid-free streams leaving adsorption columns 161 and 163 are directed through valve 219a, and subsequently undergo a pressure reduction to drop out impurities. The solvent streams then proceed to the extractant cooler 181 and the SCoCoNC fluid/cosolvent reservoir 157 to be recycled.

Next, paclitaxol is eluted from the second adsorption column 163 using a fourth fluid. The fourth fluid is comprised of a SCoCoNC fluid and a polar cosolvent. The cosolvent is present at a lower concentration than the second fluid. Thus, the fourth fluid is less polar than the second fluid. Taxoids are recovered by means of pressure drop in the natural therapeutic composition separator 175. The SCoCoNC fluid/cosolvent mixture is reintroduced to extractant cooler 181 for recycle. A certain amount of cosolvent will be present in the recovered paclitaxol. This may be removed by evaporation, condensed, and recycled.

Individuals skilled in the art will recognize that the first, second, third and fourth fluids may have identical or similar SCoCoNC fluid components, or may have different SCoCoNC fluid components and operate on distinct circuits. Similarly, the second, third and fourth fluids may have identical or similar cosolvent components or may have different cosolvent components and operate on distinct circuits. The process and apparatus are amenable to additional chromatographic processes involving further fluids.

The process and apparatus are capable of isolating natural therapeutic compositions other than taxoids. For example by substituting source material containing other natural therapeutic compositions such compositions can be isolated.

EXAMPLES

A. General

HPLC grade organic solvents used were acetonitrile, chloroform, hexane, methanol and methylene chloride from Baker, and acetone from EM Science. Purified toluene (Mallinckrodt), p-anisaldehyde (Sigma), butyl paraben (Sigma) and anhydrous ethanol (Baker) were also used. Critical fluid solvents used were CP grade (98% +) carbon dioxide ($CO_2$), nitrous oxide ($N_2O$), propane ($C_3H_8$) and Freon-22 or chlorodifluoromethane ($CHClF_2$) from Associated Gas Products, Everett, Mass.

Taxol standards utilized were baccatin III (lot#330753), cephalomannine (lot #318735) and paclitaxol (lot #s 125973 and 125973-L/24) from the National Cancer Institute, and 10-deacetylpaclitaxol (lot #GS-6S-170-4), 10-deacetyl-7-epipaclitaxol (lot #GS-6S-170-3) and 7-epipaclitaxol (lot #GS-6S-172-1) from consultant Dr. David G. I. Kingston, Virginia Polytechnic Institute and State University, Blacksburg, Va. Taxol from lot #125973-L/24 contained an impurity and was not used as a standard. Stock solutions of pure standards were made up in methanol. A mixed standard was used to evaluate coelution and peak interference with different mobile phases in the isocratic and gradient modes. A relatively pure paclitaxol-cephalomannine side cut (lot #624955-1/13/0) obtained from NCI was used.

Raw materials used were freshly cut 12" stems of *Taxus media* "Hicksii" from Renkema Farms, Zelenka Nursery, Grand Haven, Mich. The needles were manually removed from the stems and dried overnight in an oven at 60° C.; the solids content of the needles was typically about 40%. The dried needles were then ground into a fine powder (70 mesh) using a Janke & Kunkel 20,000 rpm grinder. HPLC analyses of taxanes were performed on a computer controlled ternary gradient system (Model 2350 pump/Model 2360 controller with a variable wavelength (Model V4) detector, Isco, Lincoln, Nebr.) and a Rheodyne Model 7125 injector. A 15 cm, 5 micron Phenyl column was utilized with a Phenyl guard column (Rainin, Woburn, Mass.). A ternary system was used as a gradient system, in which A=60% methanol, B=40% methanol/40% acetonitrile, and C=100% methanol. The flowrate was 1.0 ml/min and the wavelength was 228 nm. This gradient provided an excellent separation between all standards, and removed baccatin III far enough from the solvent front to allow quantification in some samples. An isocratic mobile phase consisting of 55% methanol:12% acetonitrile at 1.0 ml/min and detection at 228 nm was also utilized. Our HPLC analytical techniques were validated against analyses of the paclitaxol/cephalomannine side cut by NCI and Polysciences, Inc. (Bio-Eng: 23.8% paclitaxol and 44.3% cephalomannine versus NCI: 23.8% paclitaxol and 43.6% cephalomannine).

Other analytical and preparative instruments used were: a single beam UV/VIS spectrophotometer (Hitachi, Model 100-10), a Soxhlet extractor with Friedrichs condenser and Whatman cellulose thimbles (VWR), a micro-rotary evaporator (Buchler Instruments, Model 4214-000), and a thin layer chromatography system with diphenyl and silica plates. The thin layer chromatography system proved to be much less sensitive than HPLC for natural therapeutic compositions and was thus not used to any great extent.

Usual methods for the analysis of paclitaxol incorporate an extraction with organic solvents, partitioning into methylene chloride, and determination on a phenyl column using an acetonitrile-methanol-water mobile phase. Although these systems work well for extractions from bark samples, needle samples contain compounds which coelute with paclitaxol in this reversed phase system. An analytical method using methanol extraction, methylene chloride partitioning, and mini-column cleanup was developed to quantify the influence of coeluting compounds on paclitaxol purity from absorbance data at 228 nm and 280 nm.

There are several published methods for the determination of paclitaxol in yew needles and the bark of *Taxus brevifolia*. The present examples feature an analytical method involving a simplified extraction technique, cleanup using a silica mini-column, and final quantitation using absorbance data at 228 nm and 280 nm. This method succeeds in correcting for a coeluting impurity which is not determined by previously published methods.

The HPLC system consisted of ISCO ternary gradient instrumentation (Lincoln, Nebr.) incorporating an ISCO V4 detector for routine analytical work, an ISCO S 500 detector for simultaneous quantitation at 228 and 280 nm, and a SpectraPhysics Spectra Focus Model SF101-0122 detector for generating 3-dimensional spectral scans. The silica mini-columns (01-00 SPICE Cartridges) were obtained from Rainin Instrument Company, Woburn, Mass. The silica used in column chromatography was supplied by EMScience, Cat. No. 10180-3 Silica Gel 40, 70–230 mesh.

Samples of Taxus branches were dried at 60° C. for 16–20 hours. The needles were removed from the stems, ground in a Waring blender and sieved to pass through a 70 mesh screen. Material that did not pass was reblended until a total of 90% of the sample had passed through the screen.

A ground sample (200 mg) was weighed into a 40 mL vial. Methanol (30 mL) was added and the sample was stirred overnight using a magnetic stirrer. The extract was filtered through #40 Whatman paper into a 250 mL separatory funnel containing 15 mL of water and 10 mL of methylene chloride. The extraction vessel was rinsed with 30 mL of methylene chloride and this rinsing was filtered into the separatory funnel.

The methanol-water phase was extracted with three volumes of methylene chloride (ca 50 mL each) and these extracts were transferred to a 250 mL rotary evaporation flask. Additional water or methanol was added as needed to produce or to clarify the phase separation. The extraction was continued until a total volume of 200 mL had been collected. The extract was evaporated to apparent dryness. Traces of residual water were removed by adding 20 mL of acetone followed by 25 mL of hexane and again bringing the extract to dryness. The sample was then redissolved in 8 mL of methylene chloride.

The methylene chloride solution of the extract was slowly passed through a silica mini-column and the column was washed with an additional 4 mL of methylene chloride. This washing removed waxy, nonpolar substances; the paclitaxol was contained within a green band near the top of the column. The eluant was changed to 4% acetone in methylene chloride and the elution was stopped just as the green band began to exit from the column. The eluant was then changed to 20% acetone in methylene chloride and the paclitaxol containing band was eluted from the column using two 10 mL portions of this solvent. The extract was taken to dryness using rotary evaporation and the residue was taken up in 2.00 mL of methanol.

The HPLC column was a Rainin 80-D15-C5 Microsorb 5 micron, 4.6 mm×15.0 cm phenyl bonded phase column with a 1.5 cm phenyl guard column. The mobile phase was 12% acetonitrile and 55% methanol—the remainder being water. The flow rate was 1.0 mL/min. A paclitaxol standard at a concentration of 0.050 mg/mL was prepared in methanol. The injection volumes were 10 microliters for both standards and samples. Peak heights were measured in dual channel mode at both 228 nm and 280 nm and paclitaxol was quantified using the following equation:

$$\% \text{Taxol} = 100 \times C(\text{Standard}) \times H(\text{Sample}) \times PF \; C(\text{Sample}) \times H(\text{Standard}) \quad (1)$$

where

C=concentration in mg/mL

H=peak height from the 228 nm channel and PF=Purity Factor of the paclitaxol peak calculated from A(280)/A(228) absorbance ratio in Equation 2 (See below)

Extracts of both Taxus needles and bark were prepared using classical organic phase extraction as well as supercritical fluid extraction. Analysis conducted in our laboratory using reversed phase HPLC on a phenyl column, and using single wavelength detection at 228 nm, yielded values in the range of 0.04% to 0.05% of the dry biomass for the paclitaxol content. Portions of these extracts were then submitted to the National Cancer Institute at Frederick, Md. for confirmatory analysis. Their analysis, done with an HPLC equipped with a photo-diode array detector, indicated the presence of a substance with a large absorbance at 280 nm for the needle samples. The bark samples, all of the compounds in the paclitaxol reference mixture, and pure paclitaxol did not show this coeluting compound. The discovery of this impurity prompted us to attempt its isolation so that its presence within the paclitaxol peak could be compensated for based on its spectral characteristics.

Since the interfering compound coeluted with paclitaxol in the reversed phase system, we used a normal phase system to make the separation. A 27 g sample of *Taxus media* "Hicksii" needles was extracted with methanol-toluene and chromatographed on a 22 mm×250 mm column of silica gel. A rapid separation was made and 50% acetone in methylene chloride was used to strip the paclitaxol fraction from the column. This extract was evaporated to dryness, redissolved in 9% acetone in methylene chloride, and placed on a second 22 mm×250 mm column of silica gel which had been equilibrated with 9% acetone in methylene chloride. A slow acetone gradient was begun and the acetone concentration was monitored spectrophotometrically at 270 nm.

Figure 3:
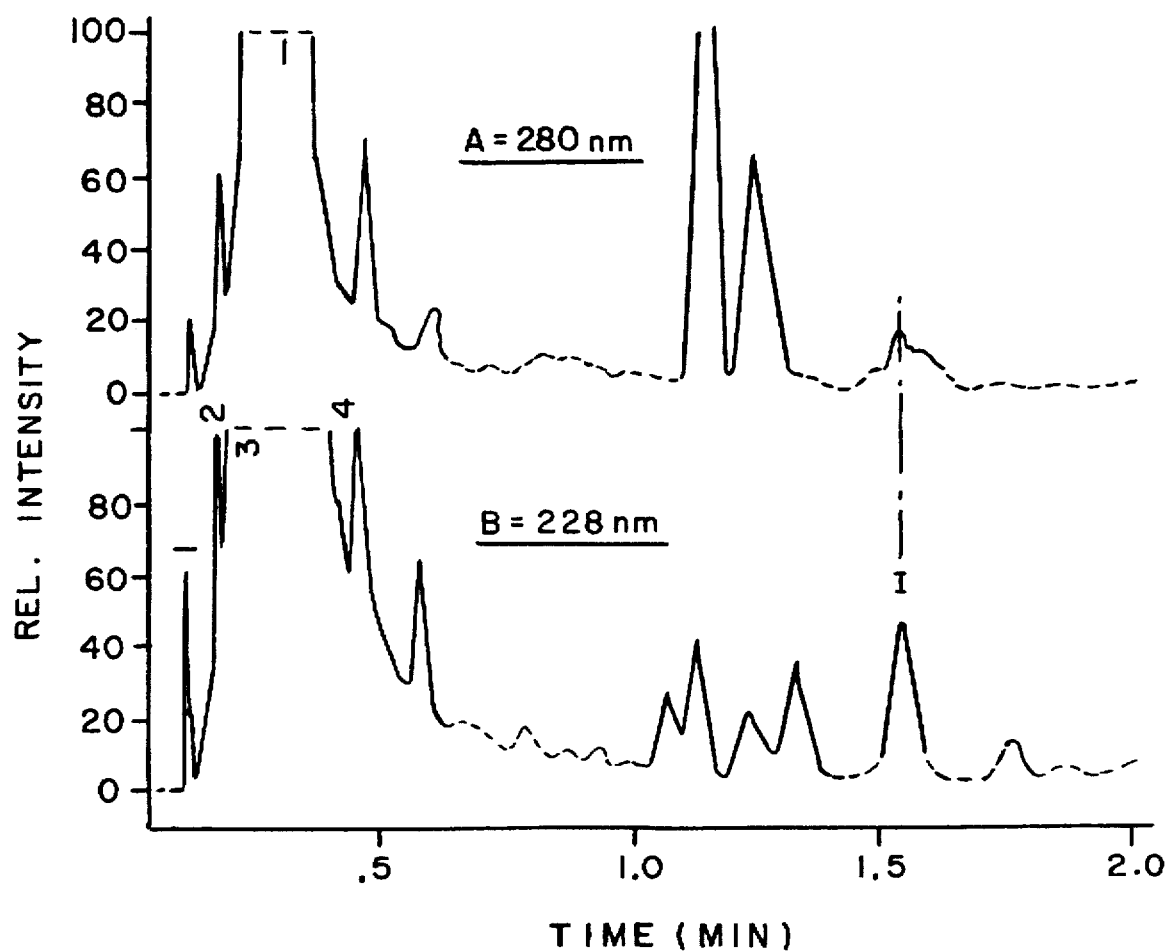
FIG. 3 depicts chromatograms of extractions from needle samples at 228 and 280 nm.

Thirteen 200 mL fractions were taken as the acetone concentration was gradually increased from 9% to 15%. Fraction #4 contained a pattern of peaks in the paclitaxol retention time region that exactly matched the pattern of peaks seen at 280 nm in the chromatographic scan of needle samples (FIGS. 3a and 3b). Spectral scans of these interfering peaks showed several common features. The interferences had absorption maxima very close to 280 nm, absorption minima close to 235 nm, and a response ratio of approximately 3.5 for A(280)/A(228).

Fraction #5 showed an absorption pattern similar to fraction #4; however, the quantity of material in this fraction was 38% that of fraction #4. Fractions #6, #7, and #8 showed decreasing mass with the same chromatographic pattern. Fraction #8 has essentially no mass. Taxol first appeared in fraction #9 as a large peak with only a small quantity of cephalomannine. Fraction #10 contained large peaks of both paclitaxol and cephalomannine. These paclitaxol fractions showed spectral scans identical to that of pure paclitaxol and yielded a value of approximately 0.05 for A(280)/A(228).

Simultaneous equations were set up to calculate the PF (Purity Factor) of the paclitaxol peak:

where

A(280)=AT(280)+AU(280)

A(228)=AT(228)+AU(228)

and A(280)=Total absorbance at 280 nm

AT(280)=Absorbance due to Taxol at 280 nm

AU(280)=Absorbance due to the Unknown at 280 nm where

K1=AU(280)/AU(228)=ca 3.50

K2=AT(280)/AT(228)=ca 0.05 and K3=A(280)/A(228)

Then $$PF = \frac{AT(228)}{A(228)} = \frac{K1 - K3}{K1 - K2}$$

Substituting in our measured values for K2 and K1, the following was obtained:

$$PF = 1.0145 - 0.29 \times A(280)/A(228) \quad (2)$$

The above formula was used to correct experimental results. Most of the samples gave an absorbance ratio of approximately 0.35 which yielded 0.91 as the purity factor. Thus, values of the paclitaxol content of the needles of the ornamental yew, *Taxus media* "Hicksii," measured to be 0.050% by reversed-phase HPLC on a phenyl column with absorbance at 228 nm were corrected to 0.046% on a dry biomass weight basis. Other workers who analyze for paclitaxol using a phenyl bonded column should be aware of the possibility that their paclitaxol peaks may contain underlying interferences and test for these interferences by running a spectral scan of the paclitaxol peak and/or monitoring at 280 nm in addition to monitoring at 228 nm.

EXAMPLES

Example 1 : Organic Phase Extractions

Several organic phase extraction techniques were employed for comparative purposes, in parallel with the critical fluid extraction and purification experiments. These techniques generically consisted of hexane washing, methanol (M)/methylene chloride (MC) extraction, three to four stages of methylene chloride-aqueous phase partitioning followed by evaporation to dryness and re-dissolution into methanol. A silica mini-column (1 cm long) was used to clean up very impure fractions prior to HPLC analysis.

First, the dry ground powder was washed with hexane to remove nonpolar waxes. Two procedures were utilized: Soxhlet extraction and mixing with a stir bar in an excess of hexane (10 ml/g) at room temperature—the latter technique is referred to as the Snader technique. The elapsed time for this procedure was between 8 to 24 hours.

The hexane extract was taken to dryness, redissolved into hexane, filtered, and cleaned up on a silica mini-column using a hexane:acetone elutant. The hexane washed needles were dried and then extracted with a 50/50 mix of M/MC. This extraction by the Soxhlet technique was conducted for 3 hours and allowed to stand for another 12 to 15 hours; in the Snader technique, the sample was allowed to spin overnight. The crude M/MC extracts were evaporated to dryness and redissolved into MC. Equal aliquots of this fraction and distilled water were mixed and then allowed to partition in a separatory funnel.

The MC phase was drained into a rotary evaporator, and the aqueous phase re-extracted with MC (up to three more times). A small amount of methanol was used to break the water/MC emulsion formed with the Snader extract. The MC partitions were dried by rotary evaporation and tared. The dried MC extract was redissolved into methanol for HPLC analysis. The results of these experiments, as a percent of initial dry biomass weight for paclitaxol and of dry extract weight for purity, are listed in Table 1.

The second sequence of experiments indicated that, as suspected, critical fluid extraction was controlled by solvent polarity. In this sequence, a sample was sequentially extracted with increasingly polar critical fluid solvents. The results of these experiments, all conducted at 3,000 psi and 60° C., are listed in Table 2.

TABLE 2

| CRITICAL FLUID EXTRACTION AS A FUNCTION OF POLARITY | | | | | |
|---|---|---|---|---|---|
| EXP # | CRITICAL FLUID | POLARITY (debyes) | DENSITY (g/ml) | TAXOL (%) | PURITY (%) |
| TAXC-4 | $CO_2$ | 0.000 | 0.738 | 0.002 | 0.013 |
| TAXC-5 | $C_3H_8$ | 0.084 | 0.495 | 0.003 | 0.029 |
| TAXC-6 | $N_2O$ | 0.200 | 0.739 | 0.003 | 0.077 |
| TAXC-7 | Freon-22 | 1.400 | 1.145 | 0.016 | 0.416 |

In Table 2 above, percent paclitaxol is based on the original dry sample mass and percent purity is based on extracted mass.

Example 3:

Several experiments were conducted to confirm and improve the Freon-22, chlorodifluoromethane ($CHClF_2$), result. For example, TAXC-7 was conducted with 10 sample volumes of Freon-22 in only 20 minutes. Several experiments were conducted to evaluate the impact of volumetric throughput and residence time on extraction efficiency. Experiments were also conducted to determine if the very nonpolar waxes inhibited the mass transfer of paclitaxol into the critical fluid phase. These experiments suggest that 100 sample volumes of critical fluid were more than sufficient to extract all the paclitaxol from a sample, and that polar waxes did impede paclitaxol mass transfer. Consequently, subsequent experiments were conducted with a minimum of 100 sample volumes of critical fluid solvent on either hexane-washed or supercritical fluid carbon dioxide (SCF $CO_2$) extracted needles. SCF $CO_2$, because of its nonpolarity and density at the conditions tested, behaves very much like hexane extracting about 7% of the polar waxes from the needles and no paclitaxol.

TABLE 1

| ORGANIC PHASE EXTRACTION OF TAXOL FROM NEEDLES | | | | | | |
|---|---|---|---|---|---|---|
| | SOXHLET | | | SNADER | | |
| FRACTION | % EXT. | % TAXOL | % PURITY | % EXT. | % TAXOL | % PURITY |
| HEXANE | 7.3 | 0.003 | 0.056 | 6.3 | 0.002 | .044 |
| MC PART. | 6.5 | 0.048 | 0.735 | 7.6 | 0.049 | 0.695 |
| AQ PART. | 19.9 | 0.001 | 0.005 | 28.4 | 0.000 | 0.002 |
| TOTAL | 35.2 | 0.052 | — | 42.3 | 0.051 | — |

Example 2: Critical Fluid Phase Extractions

Early experiments indicated that critical fluid extraction was impeded by the presence of water in the needles. Thus, all subsequent experiments were conducted on dry, milled needles of the ornamental yew in order to minimize mass transfer resistance and to maximize exposed surface area.

In order to replace Freon-22 which is an ozone depleter, the polarity of SCF $CO_2$ was modified by the addition of methanol. Conditions of temperature, pressure and cosolvent were selected on the basis of a Hildebrand solubility parameter match to Freon-22 at 3,000 psig and 60C. The results of these experiments are listed in Table 3.

TABLE 3

EXTRACTION OF TAXOL BY SCF $CO_2$/21 MOL % METHANOL

| EXP # | PRESS. (psig) | TEMP. (C) | TIME (min) | FLOWRATE (ml/min) | EXTRACT (%) | TAXOL (%) | PURITY (%) |
|---|---|---|---|---|---|---|---|
| TAXC-21 | 3,000 | 60 | 12.7 | 3.93 | 23.55 | 0.0491 | 0.209 |
| TAXC-22 | 1,259 | 40 | 40.7 | 1.28 | 21.29 | 0.0493 | 0.231 |

These experiments, based on an organic phase extraction/HPLC analysis of the residues, extracted about 99+% of the paclitaxol available.

Example 4: Impact of Pressure and Temperature

The results of sensitivity experiments on pressure, temperature and methanol concentration are listed in Table 4.

TABLE 4

EXTRACTION OF TAXOL BY SCF $CO_2$/METHANOL

| EXP # | METHANOL (mol %) | PRESS. (psig) | TEMP. (C) | TIME (min) | FLOWRATE (ml/min) | TAXOL (%) | PURITY (%) |
|---|---|---|---|---|---|---|---|
| TAXC-23 | 20.9 | 3,080 | 22 | 12.0 | 3.53 | 0.0359 | 0.270 |
| TAXC-24 | 20.9 | 3,080 | 41 | 17.1 | 2.93 | 0.0354 | 0.236 |
| TAXC-25 | 20.8 | 2,000 | 60 | 13.4 | 3.73 | 0.0480 | 0.278 |
| TAXC-26 | 20.8 | 3,000 | 60 | 18.6 | 2.69 | .0483 | 0.240 |
| TAXC-27 | 20.8 | 5,000 | 60 | 18.6 | 2.69 | 0.0389 | 0.165 |
| TAXC-28 | 0.0 | 1,259 | 41 | 20.8 | 2.46 | 0.0000 | 0.000 |
| TAXC-29 | 6.1 | 1,259 | 40 | 13.0 | 3.93 | 0.0256 | 0.463 |
| TAXC-30 | 11.1 | 1,259 | 40 | 14.0 | 3.64 | 0.0282 | 0.426 |

The average paclitaxol content of the SCF extracts and the organic phase extracts of residues of the experiments listed in Table 4 was 0.0468±0.0022; no paclitaxol was found in the residues of TAXC-25 and 26. TAXC-29 and TAXC-30 were the closest to the Freon result. (TAXC-7 in Table 2).

Example 5: Critical Fluid Extraction and Purification

Freon-22, without the use of a polar modifier, was used to determine if a silica HPLC (Water's Microporasil) column could be used to selectively strip paclitaxol out of the critical fluid phase. The results of these experiments are listed in Table 5.

the silica HPLC column. This mass, which was eluted from the column with methanol after the experiment was completed, was assayed by reversed-phase HPLC chromatography to contain 0.626% paclitaxol. The residual concentration of paclitaxol in the critical fluid treated sample, TAXC-34R, was determined to be 0.0324% by organic phase extraction and reversed-phase HPLC analysis. The total paclitaxol content of experiment TAXC-34 was thus 0.0470% of which 31.1% was recovered with a purification factor of 13 (0.626/0.047). The data listed in Table 5 suggests that the optimal results were obtained with a 2,000 psig back pressure in TAXC-32C which recovered 34.9% of the paclitaxol with a purification factor of 35.

Example 6: Extraction and Purification With Super Critical CO2/Polar Cosolvent In order to replace Freon-22, several cosolvent systems with SCF $CO_2$ were evaluated. Methanol was no longer a cosolvent of choice because it would preferentially compete with paclitaxol for adsorption sites on the silica column. This was confirmed in silica mini-column experiments and

TABLE 5

CRITICAL FLUID EXTRACTION AND PURIFICATION OF TAXOL AS A FUNCTION OF HPLC COLUMN BACK PRESSURE

| EXP # | EXT. P (psig) | BACK P (psig) | T (C) | t (min) | Q (ml/min) | EXTRACT (%) | TAXOL (%) | PURITY (%) |
|---|---|---|---|---|---|---|---|---|
| TAXC-32C | 3,000 | 1,960 | 60 | 52.8 | 4.75 | 0.99 | 0.0171 | 1.725 |
| TAXC-33C | 3,000 | 2,569 | 60 | 67.0 | 0.75 | 2.89 | 0.0176 | 0.607 |
| TAXC-34C | 3,000 | 1,500 | 60 | 6.0 | 8.33 | 2.34 | 0.0146 | 0.626 |

The foreruns of each of these experiments were collected in a 50:50 M:MC solvent trap. In each case, no paclitaxol but a significant amount of mass was collected in the forerun. For example, 12.1% of the original dry sample mass was collected from the forerun of TAXC-34, which is designated as TAXC-34F. TAXC-34C in Table 5 refers to the material (2.3% of sample mass) which was selectively deposited onto in a later experiment with the silica HPLC column. Cosolvents evaluated were methanol, methylene chloride, acetone, butanol and ethanol, each at 10 mole % in SCF $CO_2$ at 3,000 psig and 60° C.; all experiments were conducted with a back pressure of 2,000 psig. Taxol was found in significant quantities in the foreruns of experiments with methanol and ethanol as cosolvents; the results with butanol were ambiguous.

No paclitaxol was found in the foreruns of experiments conducted with methylene chloride and acetone as cosolvents at 10 mole %. About half of the paclitaxol (0.0242%) with a purification factor of 16 was recovered from the silica column in a methylene chloride cosolvent experiment (TAXC-36C). A SCF $CO_2$/acetone experiment (TAXC-37C) yielded less paclitaxol (0.0147% with a purification factor of 15) from the silica column.

Example 7: Extraction and Purification With Gradient Chromatography

The purification factor was further improved by chromatographically eluting out materials deposited on the head of the HPLC column. Because the history and retention behavior of the silica column was unknown, a gradient approach—proceeding from low polarity to moderate polarity was chosen. The results of these experiments are listed in Table 7.

Additionally, the system was operated as close to isobaric as possible in order to minimize critical fluid recompression cost.

Figure 4A:
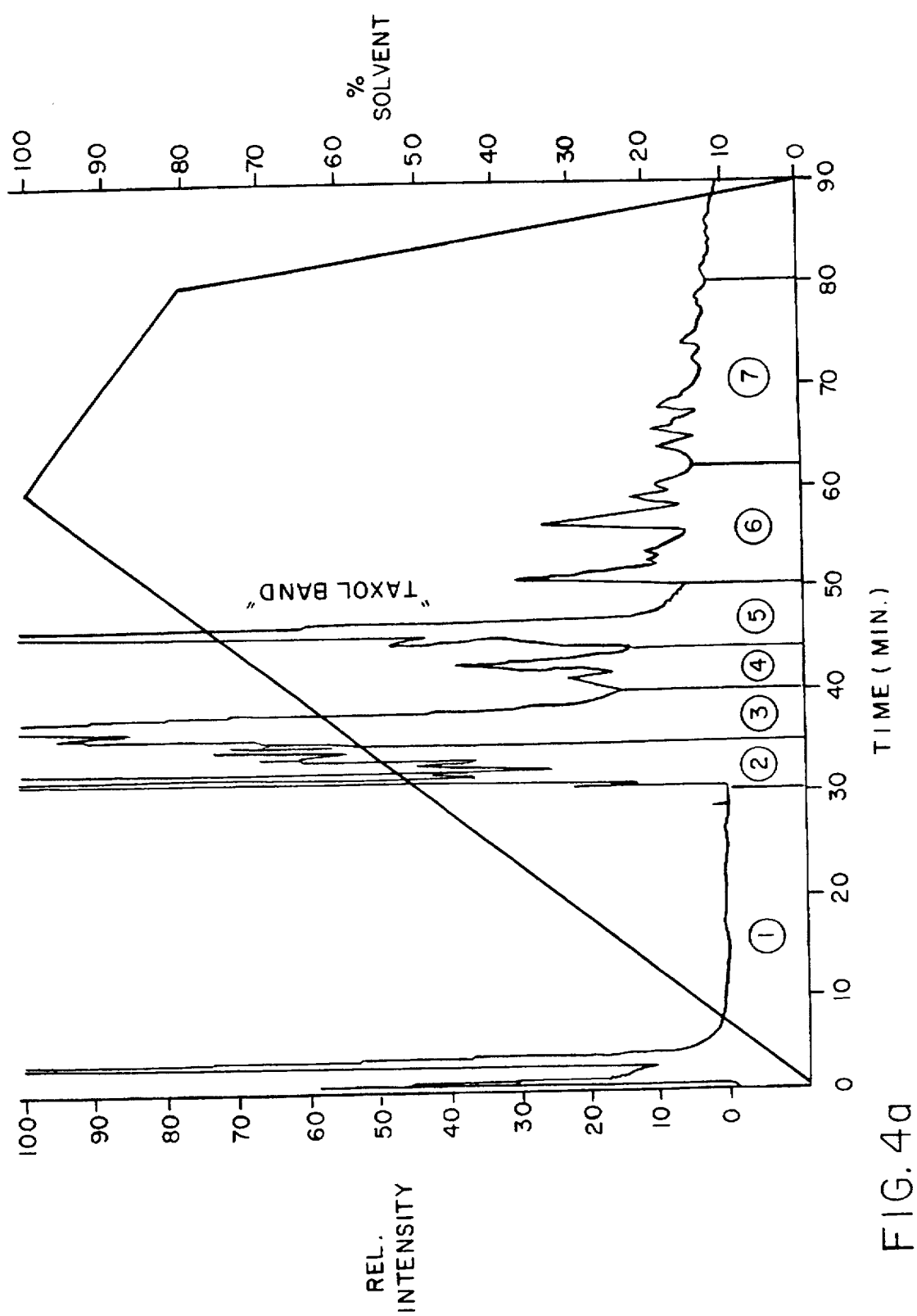
FIG. 4a and b depict chromatograms of fractions collected in accordance with a method of the present invention.
Figure 4B:
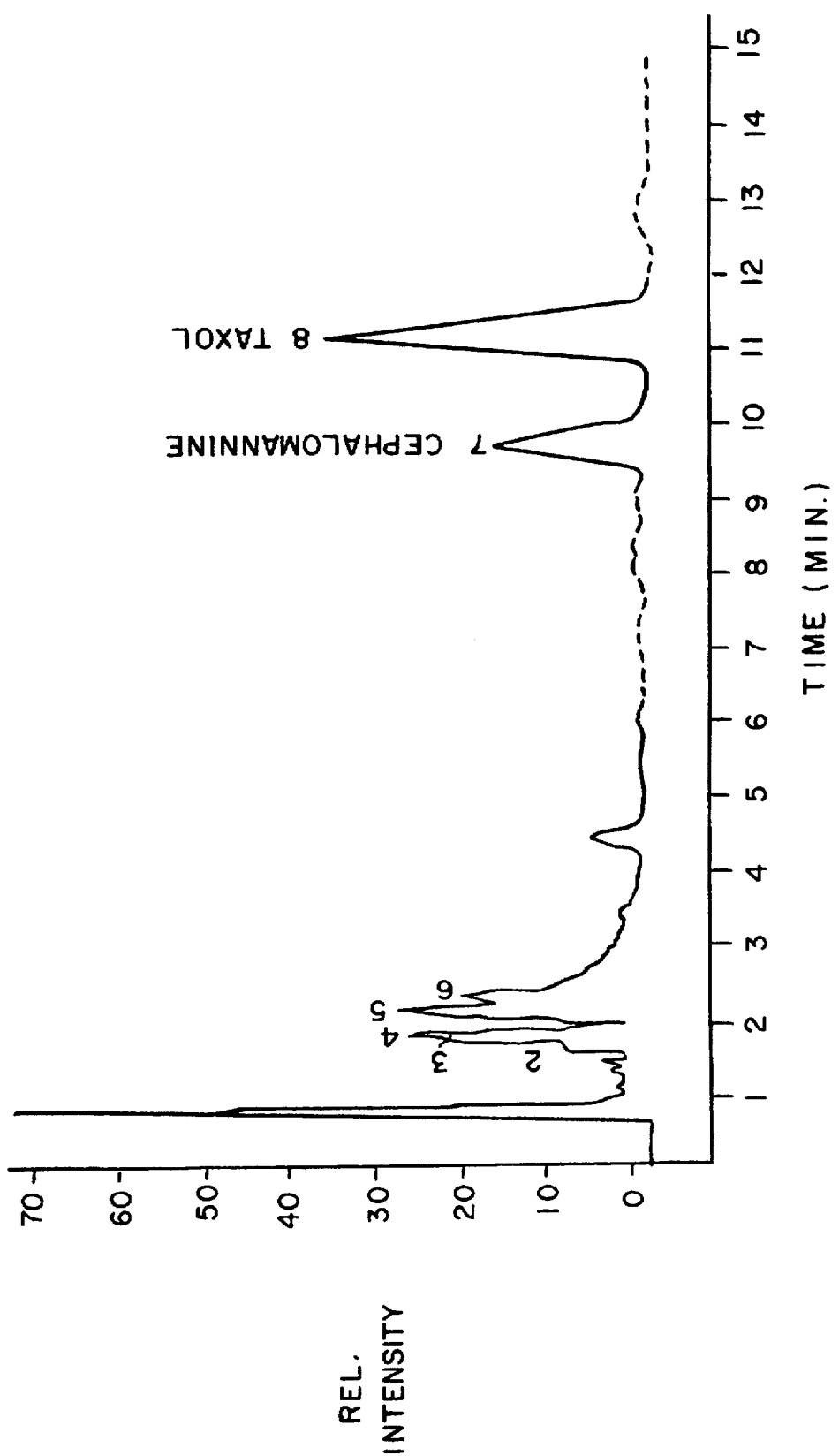

The deposited paclitaxol and other impurities were chromatographically eluted from the silica column by a hexane:n-propanol:methanol ternary gradient which was extended to obtain increased resolution of fractions. In this run, only seven fractions were taken as shown in FIG. 4a. The fractions were collected in tared vessels, brought to dryness by rotary evaporation, re-dissolved in methanol and analyzed. An HPLC chromatogram of fraction #5, the assumed "paclitaxol band," is shown in FIG. 4b. This scan indicates that the paclitaxol band contained mainly paclitaxol and cephalomannine. The purification factor was approximately 130 and the percent purity was 6.2% based on HPLC analysis and a weight of 4.0 milligrams for fraction #5.

TAXC-45C and TAXC-47C were conducted in the same manner as TAXC-43C; all three runs were preceded with an SCF $CO_2$ wash. In TAXC-45C, paclitaxol did not chromatograph off the column in a sharp peak because SCF $CO_2$ with

TABLE 6

CRITICAL FLUID EXTRACTION AND PURIFICATION OF TAXOL
AS A FUNCTION OF COSOLVENT CONCENTRATION AND PRESSURE

| EXP # | COSOLVENT | EXT. P (psig) | BACK P (psig) | TEMP (C) | TIME (min) | Q (ml/min) | TAXOL (%) |
|---|---|---|---|---|---|---|---|
| TAXC-41C | 10% ACET | 3,000 | 2,000 | 60 | 5.8 | 4.75 | 0.0171 |
| TAXC-43C | 10% ACET | 2,000 | 1,650 | 41 | 25.0 | 2.00 | 0.0200 |
| TAXC-45C | 18% ACET | 2,000 | 1,585 | 41 | 40.8 | 1.23 | 0.0200 |
| TAXC-47C | 21% MC | 2,000 | 1,650 | 40 | 25.0 | 2.00 | 0.0200 |

The percent paclitaxol recovered from the silica column was determined by the difference between total paclitaxol (an average of 0.047±0.0025% from seven experiments, TAXC-34 to 40) and paclitaxol in the biomass residues; no paclitaxol was seen in the foreruns. TAX-41C was chromatographically eluted with a hexane:methylene chloride:methanol gradient at a flowrate of 1.0 ml/min for 60 minutes. Twenty-five fractions were collected in tared vessels using absorbance at 228 nm as a guide; the collection vessel was changed at each valley in the chromatographic scan. The fractions were evaporated to dryness and weighed to determine extract weight. The fractions were then re-dissolved in a suitable quantity of methanol for conventional HPLC analysis on a reversed-phase phenyl column. A chromatogram of an assumed "paclitaxol band" indicated that this fraction was made up primarily of paclitaxol and cephalomannine. Analysis of adjacent bands indicate that about 95% of the paclitaxol had eluted in the assumed "paclitaxol band." The purity of paclitaxol could not be ascertained because of the small amount of mass recovered; the purity was, however, estimated to be about 17% yielding a purification factor of approximately 360.

TAX-43C in Table 6 differs from TAX-41C by its critical fluid extraction, selective deposition and chromatographic elution conditions. For TAX-43C, a non-hexane washed sample was first extracted with 100 sample volumes of SCF $CO_2$ at 2,000 psig and 40C (TAXC-42) to remove waxes and other nonpolar constituents. The extract, which was 6.6% of the sample dry mass, contained no paclitaxol. The residue from TAXC-42 was then extracted with SCF $CO_2$ containing 10 mole % acetone in TAXC-43. This extraction was conducted at 2,000 psig and 41C, conditions which would minimize capital and operating costs of a commercial unit.

18 mole % acetone was polar enough to spread paclitaxol over the length of the column. This was independently confirmed in experiments with a silica mini-column. In TAXC-47C, a high concentration of methylene chloride (21 mole %) in SCF $CO_2$ was effective in retaining paclitaxol at the head of the HPLC column but was not as effective as a 21 mole % methanol cosolvent in extracting paclitaxol from the raw biomass. The critical fluid extraction and chromatographic purification process described herein appears to be selective for paclitaxol over cephalomannine. The concentration of paclitaxol to cephalomannine in fraction #5 of TAXC-43C (see FIG. 4b) is 2.22 while the ratio in the needles was measured to be 1.08. Similar T/C ratios were obtained for TAXC-45C (2.04) and TAXC-47C (2.08).

Examination of the extract from SCF $CO_2$ washed samples and the foreruns of TAXC-43, 45 and 47 indicate that 10-deacetyl baccatin III and baccatin can be effectively separated from some of the polar solubles and paclitaxol. We have discovered that these baccatins are very soluble in SCF $CO_2$ with a polar cosolvent at the conditions tested and can be selectively adsorbed onto a silica column at conditions of high polarity (greater than 20% acetone—conditions which favor its extraction and purification by critical fluids.

Example 8: General Methods for Michellamine B

HPLC grade organic solvents were acetonitrile, ethyl acetate, hexane, methanol and methylene chloride from Baker, and acetone from EM Science, and purified toluene (Mallinckrodt), and anhydrous alcohol (Baker). Supercritical fluid solvents were CP grade (98%+) carbon dioxide ($CO_2$), propane, (C3H8) and Freon-22 or chlorodifluoromethane (CHClF2) from Associated Gas Products, Everett, Mass.

The biomass from *Ancistrocladus korupensis* was logged in and stored at room temperature. As needed, the leaves were ground in a Waring blender and sieved through an 80 mesh (180 μm)screen. Quantitative extractions on each ground batch were made to establish a baseline of values for michellamine-B content. Standards utilized were obtained from the NCI-Lot No. 661755-I/G of michellamine-B diacetate (MW=877).

HPLC analyses were performed using a Waters 501 HPLC pump, a 717 Autosampler, and a 996 Photodiode Array Detector, the aforementioned being controlled by the Waters Millenium™ software (V. 2.0) running on an NEC computer (486/33i). Original analytical methodology for the determination of michellamine-B in the dried leaf was provided by the NCI. This methodology, developed by Hauser Chemical Company, Boulder, Colo., utilized a 4N6 mm×100 mm, 3 μm Curosil B column (Phenomenex) with a mobile phase consisting of a 20:35:40 mixture of acetonitrile:buffer:methanol where the buffer is composed of 0.1N ammonium formate adjusted to pH 4.0 with acetic acid. Assays were performed by injecting 10 μl standard or crude extract into the mobile phase flowing at 1.0 ml/min with detection at 254 nm. This system produced extensive peak tailing. Michellamines A and B could not be resolved in the standard scans, and fast moving impurities could not be resolved from michellamine-B in sample scans of crude extracts.

To obtain better chromatographic scans and peak separation, the 10 cm, 3 μm Curosil column was replaced with a 15 cm, 5 μm pentafluorophenyl column (Keystone Scientific Company). Water was added to the mobile phase to reduce the acetonitrile concentration from 20.0% to 15.2% and the methanol concentration from 40.0% to 18.7%. 20 ml of buffer consisting of 40% triethylamine and 20% phosphoric acid (% v/v) was added to each liter of mobile phase to buffer the mobile phase to a pH of 4.4. Assays were performed by injecting 10 μl standard or crude extract into the mobile phase flowing at 1.0 ml/min with detection at 235 nm. Using this system, tailing of michellamine-B was minimized and excellent peak resolution was obtained.

Example 9: Organic Phase Extractions of Michellamine B

For the initial organic phase extractions, quantitation procedures developed by the NCI (McCloud et al., 1994) were utilized. Finely ground dried biomass was sequentially extracted twice with methylene chloride to remove oils and waxes. The dewaxed sample was then sequentially extracted twice with a 50:50 mixture of methanol:methylene chloride which removed the michellamines and green pigments. This extract was evaporated to dryness, dissolved in a 9:1 methanol:water mixture, and placed on a Bakerbond SPE Octadecyl (C18) cartridge, which had been prepared by first washing with the 9:1 methanol:water mixture, to separate the green pigments from the michellamines. The michellamines were then eluted with a 9:1 mixture of methanol:water. Initial results gave assay values of 0.58 wt. %, 0.67 wt. %, and 0.75 wt % of the dried biomass. These values appeared low with poor duplication.

To observe the distribution of mass and michellamine-B with variation in solvent polarity, a large sample weight of 3.68 grams was extracted with a series of solvents of increasing polarity. In this procedure, the sample was stirred with 200 ml of warm solvent in a 250 ml Erlenmeyer flask for a minimum of 30 minutes, was allowed to cool to room temperature, and was filtered through a 0.47 micron NylaFlo nylon membrane filter. The filtrate was transferred to a rotary evaporation flask and the biomass was rinsed with an additional 100 ml of the same solvent. The rinsings were also transferred to the rotary evaporation flask and the extract was evaporated to dryness. The dried extract was brought to 20 mL with solvent of similar polarity. To extract the biomass with the next solvent, this solvent was transferred to a wash bottle and was used to rinse the biomass from the 0.45 micron filtration unit back into the original 250 ml extraction flask. The flask was brought to 200 ml with the solvent and the process was repeated. Using this technique, the biomass was thoroughly extracted with solvent 1 before moving to solvent 2.

The results of this sequential organic phase extraction yielded a michellamine B content of 1.04 wt % of the dry biomass, are listed in Table 8.

TABLE 7

RESULTS OF SEQUENTIAL ORGANIC ANALYSIS

| Fraction | Solvent | Extraction Time | MicB (mg) | Solids (mg) | Absolute Purity (%) |
|---|---|---|---|---|---|
| 1 | Hexane | 3 hours | 0.00 | 89.2 | 0.0 |
| 2 | MC | 16 hours | 0.00 | 57.0 | 0.0 |
| 3 | 10% MeOH/MC | 30 minutes | 10.88 | 100.0 | 10.9 |
| 4 | 50% MeOH/MC | 30 minutes | 19.68 | 83.2 | 23.7 |
| 5 | 100% MeOH | 30 minutes | 7.68 | 49.2 | 15.6 |
| Totals | | 21.5 hours | 38.24 | 378.6 | 10.1 |

Even though the biomass was extracted for 16 hours with methylene chloride, no michellamine-B was extracted by the methylene chloride. Instead, the major peak was a small amount of an impurity, called A/B, having an absorbance maximum at 250 nm and a retention time (11.4 minutes) intermediate between that of michellamine-A (9.8 minutes) and michellamine-B (12.8 minutes). The 11.4 minute impurity had been completely extracted with the 10% meOH/MC and does not appear in these higher polarity extracts.

The absence of michellamine-B in the methylene chloride extract suggests that methylene chloride—or perhaps a sCoCoNC fluid with a Hildebrand Solubility parameter matching that of methylene chloride—can be used to dewax the sample before extracting with a higher polarity solvent. The presence of michellamine-B in the 100% methanol extract shows that extraction of the dewaxed sample with 50:50::methanol:methylene chloride (meom:mc) was incomplete. The extract with 100% methanol contained 20% of the extracted michellamine-B and suggests that a 30 minute extraction with screen.

The extract using 100% methanol had a purity of 15.6% which is higher than the 10.9% purity of the extract obtained using 10% methanol in methylene chloride. This suggests that, with respect to the organic extraction, 100% methanol could be used to extract the dewaxed sample. A second grind was prepared and extracted in duplicate using hexane, methylene chloride, and two extractions with methanol. The results of this second sequential organic phase extraction, yielded a michellamine B content of 1.05 wt. % of the dry biomass, are listed in Table 8.

TABLE 8

RESULTS OF SECOND SEQUENTIAL ORGANIC ANALYSIS

| Fraction | Solvent | Extraction Time | MicB (mg) | Solids (mg) | Absolute Purity (%) |
|---|---|---|---|---|---|
| 1 | Hexane | 30 minutes | 0.00 | 106.6 | 0.0 |
| 2 | MC | 30 minutes | 0.00 | 47.6 | 0.0 |
| 3 | 10% MeOH/MC | 30 minutes | 2.62 | 52.6 | 5.0 |
| 4 | 50% MeOH/MC | 30 minutes | 24.0 | 105.6 | 22.7 |

TABLE 8-continued

RESULTS OF SECOND SEQUENTIAL ORGANIC ANALYSIS

| Fraction | Solvent | Extraction Time | MicB (mg) | Solids (mg) | Absolute Purity (%) |
|---|---|---|---|---|---|
| 5 | 100% MeOH | 30 minutes | 9.57 | 57.4 | 16.7 |
| 6 | 100% MeOH | 30 minutes | 2.52 | 17.4 | 14.5 |
| Totals | | 3 hours | 38.71 | 387.2 | 10.0 |

The sequential organic extraction was extended to a seventh step by extracting partially-spent biomass with a 95:5 mixture of methanol:water, slightly acidified with a few drops of glacial acetic acid. The mixture was warmed and vigorously stirred for 30 minutes and then filtered. This procedure extracted additional michellamine-B, increasing the amount extracted to 1.82% of the dried biomass.

Example 10: Selective Extraction and Purification with ScocoNC Fluid

All experiments were conducted on dry, milled leaves in order to minimize mass transfer resistance and to maximize exposed surface area. In preliminary experiments, a dried methylene chloride-methanol extract of *A. korupensis* (NCI Sample #N54619-K) was extracted with a near-critical fluid carbon dioxide/methanol mixture of increasing polarity at 3,000 psig and 30C, and at a flowrate of 5 ml/min.

No michellamine B was extracted until the methanol concentration reached 20 volume %. This fraction contained about 50% of the available michellamine B with an absolute purity of 10.9% (relative to NCI's standard). While this 15 minute extraction was quite encouraging, a significant amount of non-polar and slightly polar impurities had been removed by a previous extraction with methylene chloride and a subsequent one with a methanol/methylene chloride mixture.

In order to define selectivity, gradient SCoCoNC extraction and purification experiments with carbon dioxide and methanol were conducted on dry milled leaves of A. korupensis. Results are listed in Table 9.

TABLE 9

SCoCoNC FLUID EXTRACTION WITH A CARBON DIOXIDE/METHANOL GRADIENT

| Exp. No. | Methanol (vol %) | Press. (psig) | Temp. (C) | Mass Extracted (mg) | Mic-B Extracted (mg) | Chromat. Purity (%) | Absolute Purity (%) |
|---|---|---|---|---|---|---|---|
| MiCB-004 | 5 | 4,000 | 25 | 28.82 | 0 | 0 | 0 |
| | 10 | " | " | 19.39 | 0 | 0 | 0 |
| | 15 | " | " | 15.25 | 0 | 0 | 0 |
| | 20 | " | " | 13.24 | 0 | 0 | 0 |
| | 25 | " | " | 7.44 | 0.0814 | 62.54 | 1.09 |
| | 30 | " | " | 6.17 | 0.3132 | 78.51 | 5.08 |
| | 35 | " | " | 6.38 | 0.7809 | 81.22 | 12.24 |
| | 40 | " | " | 6.25 | 1.1037 | 79.98 | 17.66 |
| MiCB-005 | 5 | 2,000 | 35 | 9.33 | 0 | 0 | 0 |
| | 10 | " | " | 34.86 | 0 | 0 | 0 |
| | 15 | " | " | 20.24 | 0 | 0 | 0 |
| | 20 | " | " | 8.91 | 0.0229 | 100.0 | 0.26 |
| | 25 | " | " | 5.93 | 0.0715 | 43.93 | 1.20 |
| | 30 | " | " | 5.01 | 0.1734 | 56.43 | 3.46 |
| | 35 | " | " | 4.52 | 0.6627 | 74.53 | 14.66 |
| | 40 | " | " | 12.39 | 1.7834 | 76.48 | 14.39 |

These data suggest that, while lower concentrations of methanol in carbon dioxide extracted more total solids, michellamine-B was preferentially partitioned into the fractions extracted with higher concentrations of methanol in carbon dioxide. These data suggest that michellamine-B can be extracted at fairly high chromatographic and absolute purities in a single step without the use of chlorinated organic solvents.

Example 11: Extraction and Purification of Michellamine-B with SCoCoNC as a Function of Temperature and Pressure In order to evaluate the best conditions of temperature and pressure, several experiments were conducted with a gradient of carbon dioxide and methanol over a pressure range of 1,000 to 4,000 psig and a temperature range of 15 to 45C.

Figure 5:
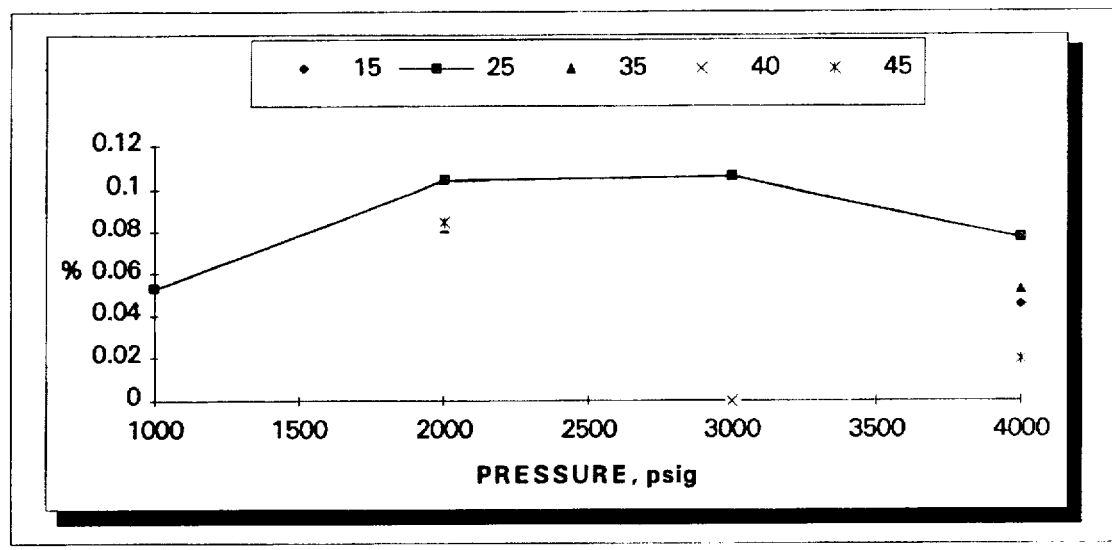
FIG. 5 depicts, in graph form, the percentage of michellamine-B extracted against isotherms by pressure.
Figure 6:
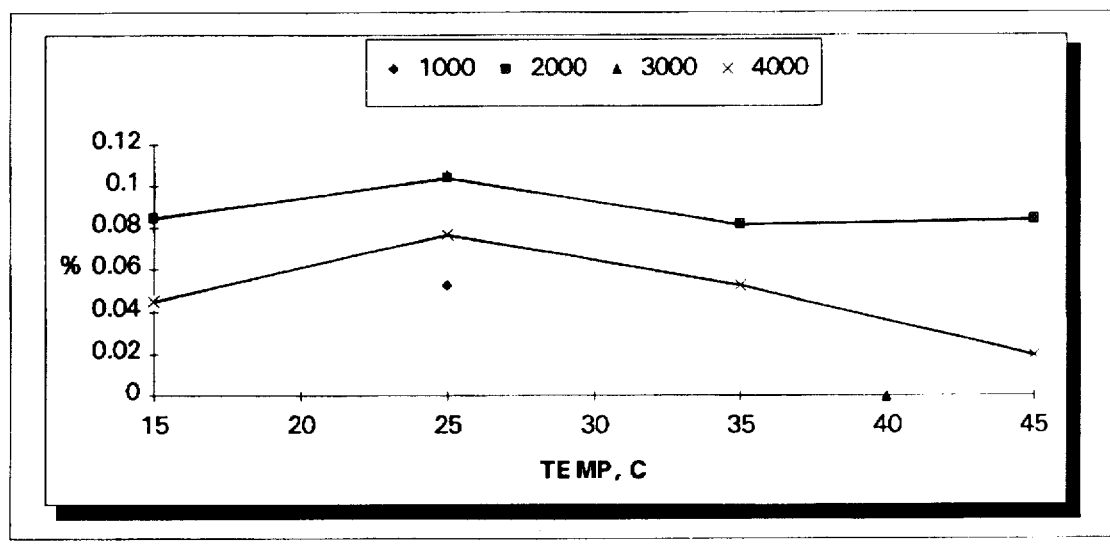
FIG. 6 depicts, in graph form, the percentage of michellamine-B extracted against isobars by temperature.

These data are depicted in graph form, in FIGS. 5 and 6. In FIG. 5 the percent michellamine-B extracted is plotted against isotherms of pressure for different temperatures. In FIG. 5, data at 15° C. is represented with closed diamonds, data at 25° C. is represented with closed squares, data at 35° C. is represented with closed triangles, data at 40° C. is represented with an "X", and data at 45° C. is represented with an X with a vertical line.

In FIG. 6 the percent michellamine-B extracted is plotted against isobars of temperature at different pressures. In FIG. 6, data at 1000 psig is represented by closed triangles, data at 2000 psig is represented by closed squares, data at 3000 psig is represented by closed triangles and data at 4000 psig is represented by "X".

Plots of total solids and michellamine B extracted as a function of methanol cosolvent concentrations in carbon dioxide indicate that the peak for extraction of solids occurs at 10% methanol and higher temperature, being relatively insensitive to the pressure. The michellamine B is not, however, drawn off until there is a high (35 to 40%) proportion of methanol in the carbon dioxide solvent.

These data suggest the most favorable extraction conditions appear to be around 2,000 psig and 25C. These data suggest that in the extraction, it would be advisable to subject the biomass first to a 10 to 20% $CO_2$/methanol wash in order to draw off the nonpolar waxes, oils, fats, and pigments, and then to extract the michellamines with a higher polarity SCoCoNC fluids at 2,000 psig and 25C.

Example 12: Multi-Step Extraction of Michellamine-B with SCoConc Fluid

This example features a comparison of a single extraction of source materials with a SCoCoNC with multiple extractions. Data is presented in Table 10 below. In Table 10, MicB-024 represents a single extraction at the parameters set forth using carbon dioxide as a critical fluid. MicB-019 represents a two-step extraction at the parameters set forth with one extraction with 10% methanol and a subsequent at 40% methanol. MicB-032 represents a multistep extraction with an initial methanol concentration of 10% and increasing stepwise through 40, 60, 80, and 100% volume.

an HPLC apparatus with a 98:2::methanol:water mobile phase, and fractions collected in equal time intervals. The michellamine B binds tenaciously to the column, as previously demonstrated on TLC plates. The mobile phase readily removed michellamine B from the column, improving the chromatographic purity from 48.3% to 61.6%, and the absolute purity from 1.9/% to 20.3% in the first fraction taken.

Since the 4.6 mm×15 cm silica column appeared overloaded, the experiment was repeated by packing a 56 mm×15 mm chamber of the ISCO supercritical extractor with silica and by using this chamber as a chromatographic column. The extract from MicB-024 was loaded onto this column by dilution with carbon dioxide so that the $CO_2$:methanol ratio was 95:5. The silica column was then eluted with a gradient of methanol in $CO_2$ at methanol proportions of 5, 10, 20, 30 and 40%, followed by a gradient of water in methanol starting at 95:5 mixtures of methanol-:water. All of the michellamine-B was retained by the column, and only about 10% was recovered in the elutants, with none in the carbon dioxide mobile phase. This experiment was repeated in MicB-030 which showed a higher recovery (81.7%) of load but no significant improvement in michellamine-B purity. Thus, while silica effectively strips michellamines from the scoconc fluid phase, its candidacy, as a solid phase matrix is impaired by poor recovery

TABLE 10

EXTRACTION WITH CARBON DIOXIDE/METHANOL GRADIENT

| Exp. No. | Methanol (vol %) | Press. (psig) | Temp. (C) | Mass Extracted (mg) | Mic-B Extracted (mg) | Chromat. Purity (%) | Absolute Purity (%) |
|---|---|---|---|---|---|---|---|
| MicB-024 | 40 | 2,000 | 25 | 5.34 | 0.163 | 52.7 | 19.8 |
| MicB-019 | 10 | 2,000 | 35 | 3.85 | 0.003 | 10.5 | 0.1 |
|  | 40 | " | " | 1.95 | 0.156 | 49.8 | 8.0 |
| MicB-032 | 20 | 2,000 | 25 | 2.93 | 0.017 | 16.0 | 0.6 |
|  | 40 | " | " | 0.95 | 0.195 | 52.6 | 20.5 |
|  | 60 | " | " | 1.51 | 10.433 | 68.0 | 28.6 |
|  | 80 | " | " | 2.86 | 0.709 | 63.4 | 24.8 |
|  | 100 | " | " | 3.97 | 0.424 | 49.9 | 10.7 |
| MicB-032 | Totals | " | " | 12.22 | 1.778 |  | 14.6 |

The single step extraction, MicB-024, yielded about 10% of the michellamine-B with relatively high purities. The single step extraction was performed in an hour. The two step extraction, MicB-019, appears less efficient which may have resulted in part from the unfavorable temperature and in part from the low methanol in CO2 wash step. MicB-032 was performed at favorable conditions with fractions of increasing methanol content. Each fraction was performed over a 20 minute interval for a total processing time of 1 hour. The high polarity gradient extraction yielded about 100% of the michellamine B with fractions containing excellent chromatographic and absolute purities. A chromatographic scan of MicB-032's 60% of methanol in CO2fraction depicted an excellent separation between michellamines B and A, and the complete absence of the A/B intermediate impurity.

Example 13: Extraction and Purification of Michellamine-B with Gradient Chromatography In MicB-023, a 4.6 mm×15 cm column house-packed with 230 mesh (<63 μm) silica from EM Science was placed in-line with the extractor at operating conditions of 2,000 psig and 25C. The column was then removed and placed on efficiencies and chromatographic purification. Better release and improved chromatographic purification will be obtained with 10% water and 90% methanol with traces of acetic acid as a mobile phase.

Aliquots from a SCoCoNC fluid extract were loaded onto the head of a C18 column with an isocratic mobile phase of 95% CO2:5% methanol extract. The columns were then eluted with a CO2:methanol gradient starting with a ratio of 95:5 and ending at 60:40. In MicB-031, in which the extractant was loaded onto the head of a 4.6 mm×30 cm C18 column, michellamines started eluting at about a 30% methanol concentration with very pure michellamine-B eluting at a 40% methanol concentration in carbon dioxide at 2,000 psig and 25C. This fraction was relatively pure, suggesting that michellamine-B could be crystallizable with very high purities from this scoconc fluid chromatographic step.

Example 14: General for Bryostatin-I

A standard, 1.00 milligrams of bryostatin-I, contained in a 2-ml, screw-cap, vial, was supplied by Dr. Russell Kirm, Department of Chemistry, College of Science, Florida Atlantic University. 2.00 mL of HPLC methanol was added to the vial, leaving about 100 mL of air-space at the top. The solution was sonicated for about 15 seconds and then capped. A 1 mL sub-sample was transferred to a 2 mL vial, was crimped shut, and was frozen. The behavior of bryostatin-I in different mobile phases is shown in Table 11.

TABLE 11

| Mobile Phase | Flow | t(R) | mAU | N |
|---|---|---|---|---|
| 100% CH3OH | 1.0 | 2.07 | 1052 | 1500 |
| 100% ACN | 1.0 | 1.92 | 1010 | 1500 |
| 95% ACN | 1.0 | 1.95 | 866 | 1080 |
| 85% ACN with 0.1% H3PO4 | 2.0 | 1.30 | 581 | 1680 |
| 90% CH3OH with 0.1% H3PO4 | 1.5 | 2.89 | 522 | 2280 |
| 85% CH3OH with 0.1% H3PO4 | 1.0 | 8.27 | 328 | 3000 |
| 82% CH3OH with 0.1% H3PO4 | 1.0 | 13.49 | 217 | 3600 |

A spectral scan was performed and indicated an absorption maxima at 262 nm and 234 nm. The maximum at 262 nm was 13% higher than the maximum at 234 nm. A acetonitrile-water system with and without 0.1% H3PO4, gives a poor peak shape and plate count. A methanol-water system gives good peak shape and plate count. Methanol in the range of 80–85% gives reasonable retention times in the methanol-water-0.1% H3PO4 Systems. For t(R)=13.5 minutes, C=0.5 mg/mL n>(264)=217 mAU.

Thus R×17/0.5=434 (about the same as Taxol)

A mobile phase system was developed for the analysis of Bryostatin I. Using a 15-cm PFP column, 82% Methanol with 0.1% H3PO4, and a flow rate of 1.0 mL/min, bryostatin I was found to elute in 13.5 minutes. The bryostatin I standard gave a spectral scan with absorption maxima matching that of literature values.

Example 14: Organic Phase Extractions of Bryostatin I

Several lots of B. Neritina were conventionally extracted and analyzed. The method is summarized in the following steps:

A biomass of dried *B. neritina* was ground. A 4 g aliquot of the ground biomass was extracted three times with 1:1 CH2CL2/CH3OH for 1 hour. This extract was deposited on 3 g celite by rotary evaporation. Dry celite was packed on top of a 2 g, 12 mL silica Prep-Pak that was flushed with hexane. This Celite/silica was eluted with 20 mL CH2Cl2, 50 mL CH3COOCH2CH3, and 50 mL CH3OH. The ethylacetate fraction was rotary evaporated and dissolved in 2 mL CH3OH. This extract was placed on the top of a 3 mL C8 column and flushed with 5 mL CH3CN. The column eluted with 10 mL CH3CN. All liquid was collected and dried. The residue was dissolved in methanol for HPLC analysis.

The results of the organic extractions are shown in the following Table 12.

TABLE 12

AMOUNT OF BRYOSTATIN-I (Mg) PER AMOUNT OF BIOMASS (g)

| Lot Number | Bryo-1 Conc. mg/g |
|---|---|
| W29 | 23.4 |
| W30 | 23.4 |
| W63 | 25.6 |

Example 15: Multistep Extraction and Purification of Bryostatin I

With the use of two (2) ISCO 260D syringe pumps and an ISCO 2-10 dual chamber extractor, supercritical fluid extractions (Byro-11,-12,-13) were performed on lot #W63H at 3000 psi and 40 degrees Celsius using a methanol/carbon dioxide step gradient. The gradient ranged from 0% methanol 100% carbon dioxide to 25% methanol 75% carbon dioxide increasing by 5% then a 50/50 fraction and finally a 100% methanol flush, except for experiment Bryo-12. In Bryolz only 0% to 15%, a 50/50 fraction and a 100% methanol flush was taken. Each fraction was approximately 10 minutes long running at 10 ml/min (approximately 100 mls collected). The exiting methanol/carbon dioxide stream was bubbled through a solvent trap containing methanol. The resulting solutions were rotary evaporated to dryness then dissolved in 1.5 ml of methanol and analyzed by HPLC. Lot No. WG3 was used in this and subsequent experiments. The experimental results are shown in Tables 13, 14 and 15.

TABLE 13

| Experiment No. | Methanol (Vol. %) | Amount (mg) | Extracted (mg/g) | Chromotographic Purity (%) |
|---|---|---|---|---|
| Bry-11-1 | 0.0 | 0.0 | 0.0 | 0.0 |
| Bry-11-2 | 5.0 | 65.2 | 14.4 | 32.1 |
| Bry-11-3 | 10.0 | 37.4 | 8.2 | 10.7 |
| Bry-11-4 | 15.0 | 16.7 | 3.7 | 3.5 |
| Bry-11-5 | 20.0 | 0.0 | 0.0 | 0.0 |
| Bry-11-6 | 25.0 | 0.0 | 0.0 | 0.0 |
| Bry-11-7 | 50.0 | 0.0 | 0.0 | 0.0 |
| Bry-11-8 | 100.0 | 0.0 | 0.0 | 0.0 |
| Total | — | 119.3 | 26.3 | — |

TABLE 14

| Experiment No. | Methanol (Vol. %) | Amount (mg) | Extracted (mg/g) | Chromotographic Purity (%) |
|---|---|---|---|---|
| Bry-12-1 | 0.0 | 24.7 | 4.9 | 32.7 |
| Bry-12-2 | 5.0 | 60.9 | 12.2 | 25.4 |
| Bry-12-3 | 10.0 | 28.1 | 5.6 | 6.7 |
| Bry-12-4 | 15.0 | 0.0 | 0.0 | 0.0 |
| Bry-12-5 | 50.0 | 0.0 | 0.0 | 0.0 |
| Bry-12-6 | 100.0 | 0.0 | 0.0 | 0.0 |
| Total | — | 113.7 | 22.7 | — |

TABLE 15

| Experiment No. | Methanol (Vol. %) | Amount (mg) | Extracted (mg/g) | Chromotographic Purity (%) |
|---|---|---|---|---|
| Bry-13-1 | 0.0 | 17.4 | 3.5 | 29.0 |
| Bry-13-2 | 5.0 | 62.7 | 12.5 | 26.7 |
| Bry-13-3 | 10.0 | 37.3 | 7.4 | 8.8 |
| Bry-13-4 | 15.0 | 0.0 | 0.0 | 0.0 |
| Bry-13-5 | 20.0 | 0.0 | 0.0 | 0.0 |
| Bry-13-6 | 25.0 | 0.0 | 0.0 | 0.0 |
| Bry-13-7 | 50.0 | 0.0 | 0.0 | 0.0 |
| Bry-13-8 | 100.0 | 0.0 | 0.0 | 0.0 |
| Total | — | 117.4 | 23.4 | — |

The SCoCoNC fluid extracts were pure enough to be directly analyzed by HPLC. Compared to the organic phase extraction and purification which was accomplished over an eight (8) hour period, the SCoCoNC fluid isolation was accomplished over a 30 minute period. The results are reproducible. Similar quantities of bryostatin I were isolated, 119.3 µg, 113.7 µg and 117.4 µg in Experiments Bry-11 Bry-12, and Bry-13, under similar conditions of temperature and pressure.

Example 6: Isocratic Purification and Extraction of Bryostatin I

Based on the results of Example 15 in which the bulk of the bryostatin I was located in the 95:5, $CO_2$ methanol fraction, an isocratic extraction of *B. Neritina* was conducted with a 95:5 mixture of $CO_2$ and methanol after extracting lipids and waxes with 100% $CO_2$. Experimental conditions were 3,000 psig and 40° C. As in Example 13, each isocratic fraction was approximately 10 minutes long running at the flow rate of 10 mL/min. The results are listed in Table 16 below:

TABLE 16

| Experiment No. | Methanol (Vol. %) | Amount (mg) | Extracted (mg/g) | Chromotographic Purity (%) |
|---|---|---|---|---|
| Bry-15-0 | 0.0 | 0.0 | 0.0 | 0.0 |
| Bry-15-1 | 5.0 | 132.4 | 26.2 | 36.0 |
| Bry-15-2 | 5.0 | 5.2 | 1.0 | 8.3 |
| Bry-15-3 | 5.0 | 0.0 | 0.0 | 0.0 |
| Bry-15-4 | 5.0 | 0.0 | 0.0 | 0.0 |
| Bry-15-5 | 5.0 | 0.0 | 0.0 | 0.0 |
| Bry-15-6 | 5.0 | 0.0 | 0.0 | 0.0 |
| Bry-15-7 | 5.0 | 0.0 | 0.0 | 0.0 |
| Bry-15-8 | 5.0 | 0.0 | 0.0 | 0.0 |
| Total | — | 137.6 | 27.2 | |

Example 15: Extraction and Purification of Bryostatin I with Freon-22

In order to include the use of alternate SCoCoNC fluid solvents, a multistep gradient extraction was performed with Freon-22 and methanol at 3,000 psig and 40C. The gradient ranged from 0% methanol:100% Freon 22 to 25% methanol:75% Freon 22 increasing by 5% followed by a 50/50 fraction and finally a 100% methanol flush. The results of this experiment are listed in Table 17.

TABLE 17

| Experiment No. | Methanol (Vol. %) | Amount (mg) | Extracted (mg/g) | Chromotographic Purity (%) |
|---|---|---|---|---|
| Bry-16-0 | 0.0 | 98.9 | 20.8 | 35.6 |
| Bry-16-1 | 5.0 | 0.0 | 0.0 | 0.0 |
| Bry-16-2 | 10.0 | 0.0 | 0.0 | 0.0 |
| Bry-16-3 | 15.0 | 0.0 | 0.0 | 0.0 |
| Bry-16-4 | 20.0 | 0.0 | 0.0 | 0.0 |
| Bry-16-5 | 25.0 | 0.0 | 0.0 | 0.0 |
| Bry-16-6 | 50.0 | 0.0 | 0.0 | 0.0 |
| Bry-16-7 | 100.0 | 0.0 | 0.0 | 0.0 |
| Total | — | 98.9 | 20.8 | — |

This experiment was repeated with heat Freon 22 in Bry-17 at 3,000 psig and 40C. Most of the bryostatin I was again extracted in the first fraction (in 10 minutes) having a chromatographic purity of 33.1%.

What is claimed is:

1. A method of extracting natural therapeutic compositions from source materials comprising the steps:
   a) dewaxing, defatting or deoiling the source material by subjecting said source material to first fluid, which first fluid is comprised of a supercritical, critical or near critical fluid, said waxes, fats and oils dissolving in the first fluid to form a wax, fat or oil laden extractant and a dewaxed, defatted or deoiled source material;
   b) subjecting said dewaxed, defatted or deoiled source material to a second fluid said second fluid comprising a critical or near critical fluid and a polar cosolvent, to form an extractant containing said natural therapeutic composition and waste material;
   c) separating said natural therapeutic composition from impurities in said extractant through chromatography means to produce a natural therapeutic composition and an eluant.

2. The method of claim 1 wherein said chromatography means comprises at least one column.

3. The method of claim 2 wherein said chromatography means comprises a first column and a second column, said first column comprising a normal phase silica adsorption column for retaining said natural therapeutic composition and said second column comprising a reverse phase adsorption column for separating or purifying said natural therapeutic composition.

4. The method of claim 3 wherein said wax, or fat, or oil laden extractant is received by said first column, said first column retaining said natural therapeutic composition which elute in critical or near critical fluid/cosolvent mixtures.

5. The method of claim 4 wherein said extractant is received by said first column, said first column retaining said natural therapeutic composition and releasing said natural therapeutic composition which elute in critical or near critical fluid cosolvent mixtures to form a first natural therapeutic composition eluant, said first natural therapeutic composition eluant depressurized to produce a natural therapeutic composition and a supercritical, critical or near critical fluid/cosolvent mixture.

6. The method of claim 5 wherein said natural therapeutic composition retained in said first column are eluted from the column with a third fluid to form a second eluant, said third fluid comprising a mixture of a critical or near critical fluid and a polar cosolvent, said polar cosolvent present of greater polarity compared to said second fluid.

7. The method of claim 6 wherein said second eluant is directed to said second column, said second column retaining said natural therapeutic composition and releasing a mixture of a critical or near critical and cosolvent.

8. The method of claim 7 wherein said natural therapeutic composition retained by said second column are eluted with a fourth fluid to form a natural therapeutic composition eluant, said fourth fluid comprising a mixture of a critical or near critical fluid and a polar cosolvent, said cosolvent present in a concentration less than said second fluid.

9. The method of claim 8 wherein said natural therapeutic composition eluant is depressurized to form said natural therapeutic composition and a mixture of a supercritical, critical or near critical fluid and cosolvent mixture substantially free of said natural therapeutic composition.

10. The method of claim 5, 7, or 9 wherein said mixtures of supercritical, critical or near critical fluid and cosolvent are recycled after said natural therapeutic composition is removed.

11. The method of claim 3 wherein said supercritical, critical or near critical fluid and cosolvent are recycled until said natural therapeutic composition elutes from said first column and thereafter directed to a second column, said natural therapeutic composition being removed by said second column to produce a supercritical, critical or near critical fluid/cosolvent mixture substantially free of said natural therapeutic composition.

12. The method of claim 11 wherein said natural therapeutic composition free supercritical, critical or near critical fluid/cosolvent mixture is depressurized allowing impurities to leave the solution to produce a critical or near critical fluid/cosolvent mixture substantially free of said natural therapeutic composition.

13. The method of claim 5 wherein said natural therapeutic composition is eluted from a first column.

14. The method of claim 5 wherein said purified natural therapeutic composition produced upon depressurization is selected from the group consisting of vincristine, vinblastine, camptothecin, michellamine-B, bryostatin-I, halomon, etopside, teniposide, ecteinascidin and closely related compositions.

15. The method of claim 9 wherein said natural therapeutic composition produced upon depressurization is selected from the group consisting of michellamine-B and bryostatin-I.

16. The method of claim 5, 7, or 9 wherein said supercritical, critical or near critical fluid and cosolvent mixture is passed through an extractant cooler to form a purified supercritical, critical or near near critical fluid and cosolvent which is recycled.

17. The method of claim 1 wherein said cosolvent is a polar solvent selected from the group of polar solvents consisting of methanol, ethanol, butanol, propanol methylene chloride and acetone.

18. The method of claim 1 wherein said supercritical, critical or near critical fluid is comprised of one or more gases selected from the group consisting of carbon dioxide, fluoronated hydrocarbons and nitrous oxide.

19. The method of claim 1 wherein said natural therapeutic composition is selected from one or more compositions consisting of vincristine, vinblastine, camptothecin, michellamine-B, bryostatin-I, halomon, etopside, teniposide, ecteinascidin and closely related compositions.

20. The method of claim 1 wherein said source material comprises needles, leaves, stems, roots, bark, seeds, flowers, and other plant parts, anatomical features of animals, protozoans and microorganisms.

21. The method of claim 12 wherein said natural therapeutic compositions are eluted from said second column with a supercritical, critical or near critical fluid and a polar cosolvent mixture to form a natural therapeutic composition laden extractant, said natural therapeutic composition laden extractant subjected to depressurization and heat to separate said natural therapeutic composition from said eluant.

* * * * *